(12) United States Patent
Leo et al.

(10) Patent No.: US 9,237,920 B2
(45) Date of Patent: Jan. 19, 2016

(54) METHOD AND APPARATUS FOR CONTROLLING LESION SIZE IN CATHETER-BASED ABLATION

(71) Applicant: Endosense SA, Meryin (CH)

(72) Inventors: Giovanni Leo, Cologny (CH); Dipen Shah, Geneva (CH); Hendrik Lambert, Geneva (CH)

(73) Assignee: St. Jude Medical Luxembourg Holding S.À.R.L., Luxembourg (LU)

( * ) Notice: Subject to any disclaimer, the term of this patent is extended or adjusted under 35 U.S.C. 154(b) by 146 days.

(21) Appl. No.: 14/160,108

(22) Filed: Jan. 21, 2014

(65) Prior Publication Data

US 2014/0194869 A1 Jul. 10, 2014

Related U.S. Application Data

(62) Division of application No. 12/776,762, filed on May 10, 2010, now Pat. No. 8,641,705.

(60) Provisional application No. 61/176,519, filed on May 8, 2009, provisional application No. 61/176,853, filed on May 8, 2009, provisional application No. 61/177,180, filed on Jun. 10, 2009.

(51) Int. Cl.
*A61B 18/14* (2006.01)
*A61B 18/08* (2006.01)
(Continued)

(52) U.S. Cl.
CPC ............... *A61B 18/082* (2013.01); *A61B 5/103* (2013.01); *A61B 5/6885* (2013.01);
(Continued)

(58) Field of Classification Search
CPC ........... A61B 2018/00357; A61B 2018/00839; A61B 18/082; A61B 5/6885; A61B 2019/504
USPC ...................................................... 606/34, 41
See application file for complete search history.

(56) References Cited

U.S. PATENT DOCUMENTS

| 5,233,515 A | 8/1993 | Cosman |
|---|---|---|
| 5,423,811 A | 6/1995 | Imran et al. |

(Continued)

FOREIGN PATENT DOCUMENTS

| CN | 101309651 | 11/2008 |
|---|---|---|
| EP | 2047797 | 9/2009 |

(Continued)

OTHER PUBLICATIONS

Watanabe, et al. "Abstract", (2002), Tokyo, Japan, 1 pg.

(Continued)

*Primary Examiner* — Ronald Hupczey, Jr.
*Assistant Examiner* — Thomas Giuliani
(74) *Attorney, Agent, or Firm* — Dykema Gossett PLLC

(57) ABSTRACT

A method and apparatus that utilizes a force-time integral for real time estimation of lesion size in catheter-based ablation systems. The apparatus measures the force exerted by a contact ablation probe on a target tissue and integrates the force over an energization time of the ablation probe. The force-time integral can be calculated and utilized to provide an estimated lesion size (depth, volume and/or area) in real time. The force-time integral may also account for variations in the power delivered to the target tissue in real time to provide an improved estimation of the lesion size. In one embodiment, the force metric can be used as feedback to establish a desired power level delivered to the probe to prevent steam popping.

30 Claims, 12 Drawing Sheets

(51) Int. Cl.
*A61B 5/103* (2006.01)
*A61B 5/00* (2006.01)
A61B 19/00 (2006.01)
A61B 18/00 (2006.01)

(52) U.S. Cl.
CPC ........ *A61B 18/1492* (2013.01); *A61B 19/2203* (2013.01); *A61B 2018/00351* (2013.01); *A61B 2018/00839* (2013.01); *A61B 2019/464* (2013.01); *A61B 2019/465* (2013.01); *A61B 2019/504* (2013.01); *A61B 2218/002* (2013.01); *A61B 2562/0261* (2013.01); *A61B 2562/0266* (2013.01)

(56) References Cited

U.S. PATENT DOCUMENTS

| | | |
|---|---|---|
| 5,437,662 A | 8/1995 | Nardella |
| 5,454,370 A | 10/1995 | Avitall |
| 5,486,161 A | 1/1996 | Lax et al. |
| 5,540,681 A | 7/1996 | Strul et al. |
| 5,542,915 A | 8/1996 | Edwards et al. |
| 5,542,916 A | 8/1996 | Hirsch et al. |
| 5,599,294 A | 2/1997 | Edwards et al. |
| 5,688,267 A | 11/1997 | Panescu et al. |
| 5,735,846 A | 4/1998 | Panescu et al. |
| 5,843,075 A | 12/1998 | Taylor |
| 5,860,974 A | 1/1999 | Abele |
| 5,868,737 A | 2/1999 | Taylor et al. |
| 5,871,523 A | 2/1999 | Fleischman et al. |
| 5,971,980 A | 10/1999 | Sherman |
| 6,001,093 A | 12/1999 | Swanson et al. |
| 6,013,074 A | 1/2000 | Taylor |
| 6,030,382 A | 2/2000 | Fleischman et al. |
| 6,039,731 A | 3/2000 | Taylor et al. |
| 6,052,618 A | 4/2000 | Dahlke et al. |
| 6,056,745 A | 5/2000 | Panescu et al. |
| 6,129,724 A | 10/2000 | Fleischman et al. |
| 6,287,306 B1 | 9/2001 | Kroll et al. |
| 6,322,558 B1 | 11/2001 | Taylor et al. |
| 6,447,506 B1 | 9/2002 | Swanson et al. |
| 6,488,678 B2 | 12/2002 | Sherman |
| 6,517,536 B2 | 2/2003 | Hooven et al. |
| 6,584,360 B2 | 6/2003 | Francischelli et al. |
| 6,696,844 B2 | 2/2004 | Wong et al. |
| 6,989,010 B2 | 1/2006 | Francischelli et al. |
| 7,048,734 B1 | 5/2006 | Fleischman et al. |
| 7,137,980 B2 | 11/2006 | Buysse et al. |
| 7,151,964 B2 | 12/2006 | Desai et al. |
| 7,163,534 B2 | 1/2007 | Brucker et al. |
| 7,282,049 B2 | 10/2007 | Orszulak et al. |
| 7,306,593 B2 * | 12/2007 | Keidar .................. A61B 5/06 606/34 |
| RE40,388 E | 6/2008 | Gines |
| 7,465,300 B2 | 12/2008 | Arless et al. |
| 7,850,685 B2 | 12/2010 | Kunis et al. |
| 8,075,498 B2 | 12/2011 | Leo et al. |
| 8,182,433 B2 | 5/2012 | Leo et al. |
| 8,409,191 B2 | 4/2013 | Avitall |
| 8,437,832 B2 | 5/2013 | Govari |
| 8,926,604 B2 | 1/2015 | Govari |
| 2005/0177151 A1 | 8/2005 | Coen et al. |
| 2005/0256522 A1 | 11/2005 | Francischelli et al. |
| 2006/0095030 A1 | 5/2006 | Avitall et al. |
| 2007/0060847 A1 | 3/2007 | Leo et al. |
| 2007/0093806 A1 | 4/2007 | Desai et al. |
| 2007/0208333 A1 | 9/2007 | Uchida et al. |
| 2008/0009750 A1 | 1/2008 | Aeby et al. |
| 2008/0097220 A1 | 4/2008 | Lieber et al. |
| 2008/0161793 A1 | 7/2008 | Wang et al. |
| 2008/0275440 A1 | 11/2008 | Kratoska et al. |
| 2008/0294144 A1 | 11/2008 | Leo et al. |
| 2009/0138007 A1 | 5/2009 | Govari |
| 2009/0177111 A1 | 7/2009 | Miller et al. |
| 2009/0306643 A1 | 12/2009 | Pappone et al. |
| 2010/0041986 A1 | 2/2010 | Nguyen |
| 2010/0168738 A1 * | 7/2010 | Schneider .......... A61B 18/1206 606/41 |
| 2012/0209260 A1 | 8/2012 | Lambert et al. |

FOREIGN PATENT DOCUMENTS

| | | |
|---|---|---|
| WO | 2007001981 | 1/2007 |
| WO | 2007050960 | 5/2007 |
| WO | 2007109171 | 9/2007 |
| WO | 2008045958 | 4/2008 |
| WO | 2008063195 | 5/2008 |

OTHER PUBLICATIONS

Katsuaki, Yokoyama et al., Novel contact force sensor incorporated in irrigated radiofrequency ablation catheter predicts lesion size and incidence of steam pop and thrombus, Circulation Arrhythmia and electrophysiology, pp. 354-362, Dec. 2008.

Watanabe et al., Cooled-tip ablation results in increased radiofrequency power delivery and lesion size in the canine heart: importance of catheter-tip temperature monitoring ofr prevention of popping and impedance rise, Journal of Inventional Cardiac Electrophysiology, 6, Feb. 9-16, 2002.

International Search Report and Written Opinion for PCT Application No. PCT/US2011/067391, dated Jul. 11, 2013. 4 pgs.

Ikdea, et al. "Presentation Abstract" 15841—Contact Force-Time Integral Predicts Radiofrequency Lesion Size and Incidence of Steam Pop in the Canine Beating Heart. Nov. 5, 2012. American Heart Association. 2 pgs.

Seiler, et al. "Steam pops during irrigated radiofrequency ablation: factors affecting steam popping and depth of injury in the pig liver," (2004), St. Louis, Missouri. 1 pg.

Calkins, et al. "HRS/EHRA/ECAS expert Consensus Statement on catheter and surgical ablation of atrial fibrillation: recommendations for personnel, policy, procedures and follow-up", A report of the Heart Rhythm Society (HRS) Task Force on Catherer and Surgical Ablation of the Atgrial Fibrillation. Eurospace (2007), vol. 9. pp. 335-379.

Calkins, et al. "2012 HRS/EHRA/ECAS expert consensus statement on catheter and surgical ablation of atrial fibrillation: recommendations for patient selection, procedural techniques, patient management and follow-up, definitions, endpoints and research trial design", J. Interv Card Electrophysiol. Mar. 1, 2012. 87 pages.

Pappone, et al. "Non-fluoroscopic mapping as a guide for atrial ablation: current status and expectations for the future", European Heart Journal Supplements. vol. 9, Suppplement 1, pp. 1136-1147, Dec. 2007.

Huang, et al. Catheter Ablation of Cardiac Arrythmia, Chapter I, "Catheter Ablation of Cardiac Arrythmias". Mar. 2006. 20 pgs.

Kuck "Importance of Catheter Contact Force and Stability in Radiofrequency Catheter Ablation (powerpoint presentation)", St. Georg Hospital in Hamburg, Germany, May 14, 2008. 47 pgs.

Acker, et al. "Featured Poster Session", Featured Poster, (2009), pp. S95-S120.

Kuck "First clinical data on Catheter Contact Force—impact on safety and effectiveness, (powerpoint presentation)" St. Georg Hospital in Hamburg, Germany, May 14, 2008. 30 pages.

Topp, et al. "Saline-Linked surface radiofrequency ablation: Feasibility of impedance monitoring for prevention", (Jul. 2008) 1 pg.

* cited by examiner

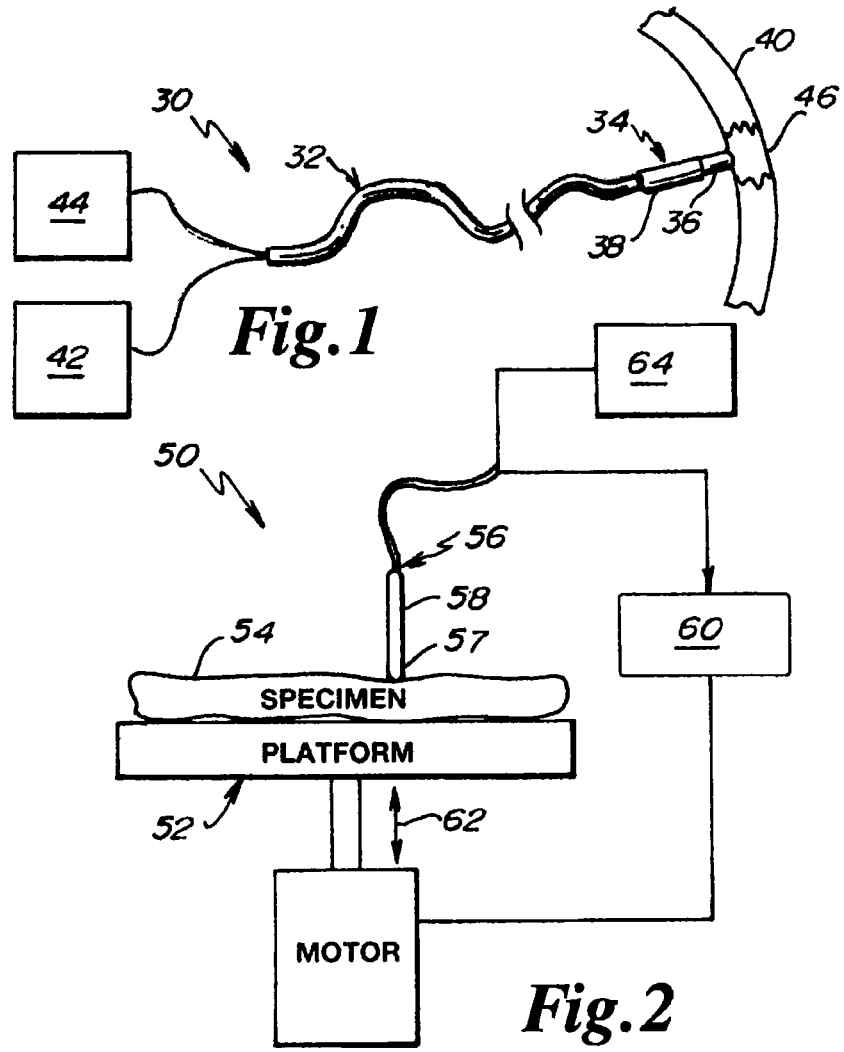
*Fig.1*
*Fig.2*
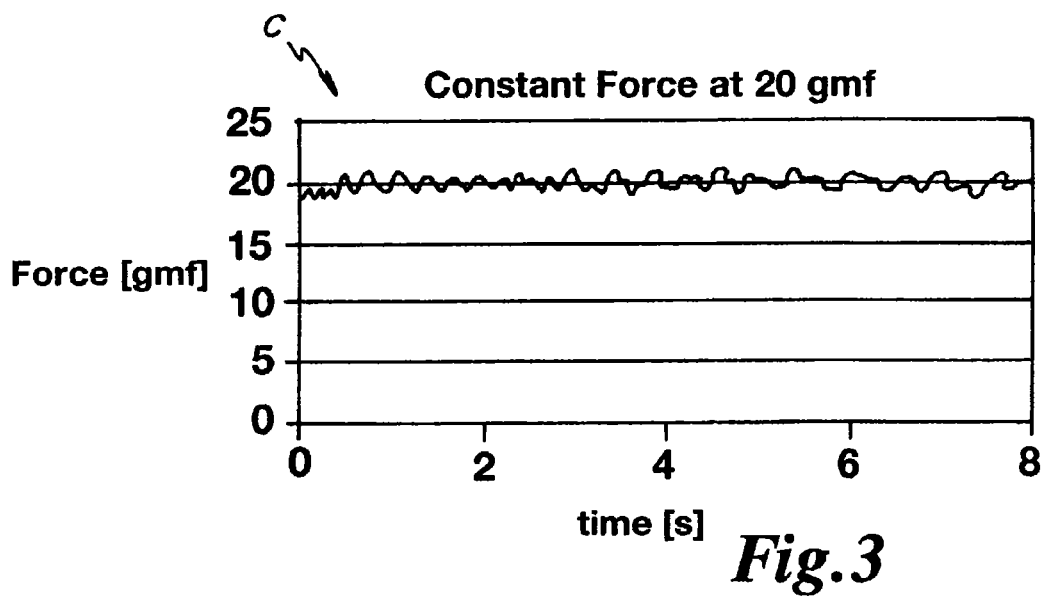
*Fig.3*

METHOD AND APPARATUS FOR CONTROLLING LESION SIZE IN CATHETER-BASED ABLATION

RELATED APPLICATIONS

This application is a divisional of U.S. patent application Ser. No. 12/776,762, filed May 10, 2010, now U.S. Pat. No. 8,641,705, which claims the benefit of U.S. Provisional Patent Application No. 61/176,519, filed May 8, 2009, of U.S. Provisional Patent Application No. 61/176,853, filed May 8, 2009, and of U.S. Provisional Patent Application No. 61/177,180, filed on Jun. 10, 2009, the disclosures of which are hereby incorporated by reference herein in their entirety except for definitions defined therein.

FIELD OF THE INVENTION

The field of the invention relates generally to the treatment of organic tissues using ablation therapy, and more specifically to the prediction and display of lesion sizes using catheter-based contact ablation delivery systems.

BACKGROUND

There are many known conditions that affect the electrical impulses that drive the normal operation of the heart. Atrial fibrillation is one common cardiac arrhythmia involving the two upper chambers (atria) of the heart. In atrial fibrillation, disorganized electrical impulses that originate in the atria and pulmonary veins overwhelm the normal electrical impulses generated by the sinoatrial node, leading to conduction of irregular impulses to the ventricles that generate the heartbeat. Atrial fibrillation can result in poor contraction of the atria that can cause blood to recirculate in the atria and form clots. Thus, individuals with atrial fibrillation have a significantly increased risk of stroke. Atrial fibrillation can also lead to congestive heart failure or, in extreme cases, death.

Common treatments for atrial fibrillation include medications or synchronized electrical cardioversion that convert atrial fibrillation to a normal heart rhythm. Surgical-based therapies have also been developed for individuals who are unresponsive to or suffer serious side effects from more conventional treatments. The surgical techniques include making incisions in the right and left atria to block propagation of the abnormal electrical impulse around the atrial-chamber.

U.S. Patent Application No. 2005/0256522 to Francischelli et al. (Francischelli) discloses a surgical-based technique for creating linear lesions along the heart wall by making an incision and inserting a jaw of a dual jawedablation head into the heart and clamping a selected portion of the heart wall between the jaws. The jaws are used to measure the thickness of the heart wall tissue. A known clamping force is applied to the jaws, from which a strain on the heart wall tissue can be inferred. Based on the thickness of the heart wall, a combination of jaw force, RF energy and ablation time is selected to fully ablate the clamped tissue. The strain imposed by the jaws is also used to infer the transmurality of the lesion.

Catheter-based contact ablation techniques have evolved as a minimally invasive alternative to surgical-based techniques, and also as an alternative for individuals who are unresponsive to or suffer serious side effects from more conventional treatments (e.g., medications). Contact ablation techniques involve the ablation of groups of cells near the pulmonary veins where atrial fibrillation is believed to originate, or the creation of extensive lesions to break down the electrical pathways from the pulmonary veins located on the posterior wall of the left atrium. Methods of energy delivery include radiofrequency, microwave, cryothermy, laser, and high intensity ultrasound. The contacting probe is placed into the heart via a catheter that enters veins in the groin or neck and is routed to the heart, thus negating the need for an incision in the heart wall from the outside. The probe is then placed in contact with the posterior wall of the left atrium and energized to locally ablate the tissue and electrically isolate the pulmonary veins from the left atrium. Where complete the electrical isolation is desired, the process is repeated to form a continuous line of ablated tissue between the left atrium and the pulmonary veins.

The advantages of contact ablation techniques have been recognized; there is no open body and thus risks of infection and recuperation time are reduced. Further, utilizing the aforementioned techniques often reduce or remove the need of pacing hardware or other forms of electronic or mechanical therapy.

However, a concern with some contact ablation techniques is a phenomenon known as "steam pop." Steam pops are a risk associated particularly with irrigated radiofrequency catheter ablation, wherein subsurface heating causes rapid vaporization and expansion that disrupts the proximate tissue and is accompanied by an audible popping sound. If the disruption is of sufficient magnitude (i.e. the volume of the vaporizing expansion large enough), cardiac perforations can lead to "tamponade," wherein blood accumulates in the space between the myocardium (the muscle of the heart) and the pericardium (the outer covering sac of the heart, causing compression of the heart.

One study concludes that maintaining catheter tip temperatures below 45° C. will prevent steam popping during RF energy delivery. See Watanabe, et al., "Cooled-Tip Ablation Results in Increased Radiofrequency Power Delivery and Lesion Size in the Canine Heart: Importance of Catheter-Tip Temperature Monitoring for Prevention of Popping and Impedance Rise," *Journal of Interventional Cardiac Electrophysiology*, vol. 6, no. 2, pp. 9-16 (2002). By contrast, another study determined that that steam pops are not related to the temperature of the contacting ablation head, but instead are a strong function of the decrease in target tissue impedance, and recommends monitoring the impedance so that it does not decrease more than a predetermined amount. See Seiler et al., "Steam pops during irrigated radiofrequency ablation: Feasibility of impedance monitoring for prevention," *Heart Rhythm*, vol. 5, no. 10, pp. 1411-16 (2008).

A draw back of impedance-based measurement to establish good ablation contact is that the organ wall may not have a uniform behavior. Fat areas have very different impedance than muscle areas. The differences make the impedance reading an unreliable indicia of contact integrity. In addition, safety may be compromised because the attending physician may exert a greater contact force to obtain a better impedance indication while not having the benefit of knowing the contact force.

Another study has concluded that steam popping can be avoided by proper selection of power level/lesion diameter combinations. See Topp et al., "Saline-linked surface radiofrequency ablation: Factors affecting steam popping and depth of injury in the pig liver," *Ann. Surg.*, vol. 239, no. 4, pp. 518-27 (2004). U.S. Patent Application Publication No. 2008/0097220 to Lieber et al. discloses a method of detecting subsurface steam formation by measuring the tissue reflection spectral characteristics during ablation.

Another concern with contact ablation techniques is whether the lesion size is sufficient to accomplish the electrical isolation. At the same time, excessive ablation is also problematic. Excessive ablation can cause damage to the tissues of other organs proximate the heart (e.g. the esophagus), and can also damage the structural integrity of the atrium and lead to "breakthrough," wherein blood leaks through the atrium wall. Techniques to control lesion size during contact ablation procedures include: an impedance measurement between the contacting probe and ground through the target tissue (WO 2008/063195, US 2008/0275440); monitoring the current output of intervening tissues (serving as an electrolyte) during RF ablation for an inflection that occurs before the onset of harmful tissue charring (U.S. Pat. No. 6,322,558); the use of external auxiliary electrodes to increase lesion depth (U.S. Pat. No. 7,151,964); a microwave probe to heat sub-surface tissue in combination with cryogenic contact cooling of the surface tissue to extend lesion depth without harming surface tissue (U.S. Pat. No. 7,465,300); measuring the temperature of the lesion immediately after energy delivery (US 2008/0275440). Several patents disclose methods for cooling and/or monitoring the temperature of the tip of an RF ablation probe to prevent overheating of the probe tip and the attendant buildup of coagulant that interferes with RF transmission, thereby enhancing lesion depth (US 2005/0177151, US 2007/0093806, US 2008/0161793).

Despite advances in the control of lesion size and steam popping, the effectiveness and risks associated with catheter-based ablation can be highly variable. See Calkins et al., "HRS/EHRA/ECAS expert Consensus Statement on catheter and surgical ablation of atrial fibrillation: recommendations for personnel, policy, procedures and follow-up. A report of the Heart Rhythm Society (HRS) Task Force on catheter and surgical ablation of atrial fibrillation". *Heart Rhythm*, v. 4, no. 6, pp. 816-61 (2007). Calkins notes that the results of catheter ablation are widely variable, due in part to differences in technique and to the experience and technical proficiency of the administering physician.

Catheter-based ablation techniques also present challenges relating to visualization of the procedures and providing the operator indications of success, problem areas or potential complications. Early methods for visualization of ablation techniques include mapping the heart cavity utilizing catheter endocardial mapping (U.S. Pat. No. 4,940,064) which relies on the analysis of electric signals. These early methods proved unreliable and more advanced methods were developed to increase the accuracy of the cavity modeling. More recent methods of visualization utilize a Computed Tomography (CT) or Magnetic Resonance Imaging (MRI) scan to first model the patient's body cavity at high resolutions followed by a "fusion" with system that establishes a relationship between the 3-dimensional image and physical coordinates. Certain systems utilize a catheter position sensor to create a morphologic map of the organ. Other systems utilize a catheter position sensor that maps the image coordinates of the CT/MRI scan with the sensed physical organ regions in the patient. Some of these systems utilize position sensors based on electrical signals while other systems utilize electromagnetic signals. Still other systems utilize ultrasound arrays to determine location in creating an accurate map of the heart cavity. Commercial mapping implementations are available including the Biosense CARTO® mapping system which utilizes magnetic field sensors and a specialized catheter to detect chamber geometry and EnSite NavX™ Navigation and Visualization Technology which utilizes electrical sensors and a standard catheter to generate 3D models. Still other methods utilize X-Ray machines mated with image fusion technologies such as XMR to generate a 3D visualization of the heart cavity.

A method with rapidly increasing interest is the 3D angiography which utilizes a contrast medium that is injected into the heart cavity. After injection, fluoroscopy equipment rotates around the patient capturing information. Based on the captured information, a computer system is able to construct a 3D rendering of the heart cavity. Recent advances in MRI technologies including Delayed-enhancement Magnetic Resonance Imaging (DE-MRI) techniques have been developed that are providing increased resolution images of the heart cavity without spatial distortion. Other recently developed 3D mapping techniques have been published by Pappone et al., "Non-fluoroscopic mapping as a guide for atrial ablation: current status and expectations for the future", *European Heart Journal Supplements*, vol. 9, Supplement I, pp. 1136-1147 (2007), which is hereby incorporated by reference in its entirety except for express definitions defined therein.

However, while 3D visualization techniques have advanced, they are only one component in the analysis of ablation procedures. Traditionally, ablation procedures have been characterized by measuring the power, temperature and/or time of the RF energy being applied. These initial characterizations proved unsuccessful in predicting overall lesion size and effectiveness. Thus, existing technology merely provides the operator with a limited amount of visual information related to their ablation procedure. Existing visualizations may provide the operator with an estimate of power, temperature and time by color coding fixed-size 3D objects overlaid onto a 3D virtualization of the heart cavity. However, there is no technology available that is able to provide an operator with a comprehensive visualization and characterization of the ablation procedure outcome.

Alternative apparatuses and methods for predicting the size of lesions and/or reducing the incidence of injurious steam pops during catheter-based contact ablation procedures, as well as for visualizing the predicted lesion sizes, tissue damage (i.e. perforations and resistive tissues) and isolation gaps during contact ablation procedures would be welcome.

SUMMARY OF THE INVENTION

Various embodiments of the invention reliably predict the volume, area and/or depth of lesions created through the use of a force-time integration technique. Other embodiments control the energy delivered to the ablation probe based on the contact force between the ablation probe and the target tissue to prevent steam popping.

In another aspect, various embodiments of the invention reliably visualize the predicted volume, area and/or depth of lesions created during ablation procedures. One embodiment visualizes the predicted lesions created utilizing a force contact density mapping procedure. Another embodiment visualizes the predicted lesions through the use of a force-time integration technique. Yet another embodiment visualizes the predicted lesions through the use of a force-time and power (and/or current) integration technique. Other embodiments predict the occurrence and locations tissue damage such as perforation that occurred during the ablation process. Still other embodiments predict the occurrence and location of isolation gaps that may occur during or after the procedure.

Recent advances in catheter-based contact ablation systems have included the ability to measure a reactive force on a catheter that results from contact with the target tissue. A number of patent applications have recently disclosed apparatuses and methods for determining the contact force or stress measurement at the distal tip when in contact with the target tissue. See, e.g., EP 2047797, WO 2008/045958, WO 2007/050960. These disclosures introduce contact force and/or contact pressure as another real-time metric that is available to the practitioner during contact ablation procedures, in addition to time, temperature, power and/or current). U.S. Patent Application Publications 2006/0200049, 2007/0060847, 2008/0294144 to Leo et al. and 2008/0009750 to Aeby et al., assigned to the assignee of the present application and the disclosures of which are hereby incorporated by reference in their entirety except for express definitions therein, disclose devices and methods for resolving a force vector in three-dimensional space for a reactive force on the end effector of a catheter, including an RF ablation head.

It has been found that integrating the reactive force over the time of contact at a known energization level can provide reliable estimates of the size of the resulting lesion. Alternatively, the product of the force and energization level, which can both vary with time, can be integrated over the time of contact. Reliable approximations to the force-time or force-energization-time integrals may also be produced by knowing the time of contact and multiplying by an average or other representative value of the force and/or energization over the time interval. Herein, a "force-time integral" is broadly defined as a measured quantity that involves the measurement of force over time. Accordingly, a "force-time integral" as used herein includes force-time products (e.g. a representative force multiplied by the time interval of application), force-energization-time integrals, force-time-energization products, and combinations thereof.

Studies regarding the relationship between the contact force and lesion size, as well as contact force and lesion size have been published by Yokoyama et al., "Novel Contact Force Sensor Incorporated in Irrigated Radiofrequency Ablation Catheter Predicts Lesion Size and Incidence of Steam Pop and Thrombus," *Circulation: Arrhythmia and Electrophysiology*, vol. 1, no. 5, pp. 354-362 (December 2008), which is hereby incorporated by reference in its entirety except for express definitions defined therein. Yokoyama also discloses the optimization of RF power and application time to maximize lesion formulation and reduce steam pop and thrombosus. Yokoyama, however, does not disclose a nexus between a force-time integrals and lesion size prediction.

Herein, an apparatus and method is disclosed for further reducing the incidence of steam pop. Structurally, the apparatus and method utilize a contact force or contact pressure measurement as a feedback element to the power source controlling the delivery of energy to the ablation head. The power level is controlled for higher output when there are low or intermittent contact forces/pressures, and for lower output when there is higher contact forces/pressure. By this technique, steam popping can be reduced.

In some embodiments, an apparatus and method is provided for comprehensively characterizing the results of ablation operation utilizing visualization technology. The visualization aspect can provide the operator with reliable indications of lesion characteristics (e.g. area, volume and/or depth) of the lesions created during ablation procedure, in real time and/or for post-operative analysis. In certain embodiments, contact density is mapped to a three-dimensional (3D) visualization of the heart cavity during the ablation procedure. In other embodiments, force, time and an ablation energization parameter (e.g. power or current) are mapped to a 3D visualization of the heart cavity during the ablation procedure.

The visualization aspects of the invention may enable the professional to increase the efficiency of the ablation procedure by making reliable approximations of lesion size and assessing the completeness of isolation lines. In still other embodiments contact, force and power density is mapped to a 3D visualization of the heart cavity. The visualization aspects may enable the operator to make reliable approximations of potential tissue damage such as perforation prone areas which may produce complications in patient recovery. The visualization aspects may further enable the operator to make reliable approximations of potential isolation gaps that are present during the procedure or may occur in a certain period after the procedure. The visualization aspects can further provide the operator with the ability to differentiate between lesions created by each surgical procedure, thus providing information as to overall coverage and patient history. Thus, information relating to ablation procedures may be stored for further analysis or to become part of the patient's medical history. Finally, some embodiments of the invention may provide information as to the creation of edemas or other cell structures that negatively affect the penetration of RF power during the ablation process. These edemas or structures may be then monitored or targeted for future ablation procedures. By utilizing the described methods and apparatus, the characteristics of lesions created during the ablation process can be predicted reliably, ensuring procedure success and potentially reducing procedure complications and recovery time.

The methods and apparatuses disclosed herein are also adaptable to robotic control of contact and/or lesion size. Calculation of the force-time integral can be performed by a microprocessor that also controls (or provides information to another microprocessor that controls) the manipulation of the catheter. The calculation can be performed in real time or pseudo-real time so that either the power output (or voltage or current output) or the contact force or contact pressure is actively controlled by the system to produce the predicted lesion size, without human intervention in the control of the force-time integral.

Structurally, various embodiments of a system for ablating a target tissue during a medical procedure comprise an elongate flexible catheter adapted to be introduced into a patient during the medical procedure, the catheter including a distal portion. An ablation head is disposed at the distal portion of the catheter, the ablation head adapted to contact the target tissue during the medical procedure. A force sensor is operatively coupled with the ablation head and adapted to detect a contact force exerted on the ablation head from contact with the target tissue, the force sensor outputting a signal in response to the contact force. In one embodiment, the force sensor includes a fiber optic strain gauge. A power source is operatively coupled with the ablation head for energization of the ablation head. A current sensor may be configured to detect the electrical current to the ablation head.

In one embodiment, a control system is adapted to receive the signal from the force sensor to produce a sequence of contact force values. The data acquisition system can also be adapted to determine a time period of energization of the ablation head and for integration of the sequence of contact force values acquired over the time period of energization to produce a force-time integral.

In one embodiment, the control system is adapted to determine an energization parameter to be delivered to the ablation head and to predict a size parameter of a lesion on the target tissue created by the energization parameter. The prediction in this embodiment is based on the force-time integral and the energization parameter. In one embodiment, the energization parameter is power level and/or electrical current. The control system can be adapted to determine the magnitude of the electrical current delivered to the ablation head, and be further adapted to predict a size parameter of a lesion on the target tissue created by the magnitude of current, the prediction being based on the force-time integral and the magnitude of current. The size parameter can be one or more of lesion volume, lesion depth or lesion area.

The control system can also be adapted to control the time period of energization of the ablation head, as well as the magnitude of an energization parameter delivered to the ablation head with the power source. In one embodiment, the control system is adapted to control the magnitude of an energization parameter delivered to the ablation head with the power source, the magnitude of the energization parameter being based on the magnitude of the contact force. The control system can be adapted to substantially disable energization of the ablation head with the power source when the force-time integral reaches a predetermined value. In still other embodiments, the control system can be adapted to increase irrigation, in addition or in place of decreasing or disabling energization. The control system in certain embodiments can be configured to calculate the force-time interval in real time.

The overall system can be configured for manual operation by a human operator, or coupled to a robotic manipulator for movement of the distal portion of the catheter. The robotic manipulator can be controlled by the control system.

In certain embodiments, the control system includes a central processor operatively coupled to the force sensor and the power source. A storage medium can be provided that contains programming instructions to be accessed and carried out by the central processor. In one embodiment, the programming instructions include measuring a sequence of contact forces with the force sensor while the ablation head is in contact with the target tissue, the sequence of contact forces being in reaction to the contact; energizing the ablation head for a period of time while the sequence of contact forces is being measured; and integrating the sequence of contact forces that were measured with the force sensor over the period of time of energizing the ablation head to determine a force-time integral. The programming instructions can further include determining an energization parameter delivered to the ablation head during the energizing of the ablation head, controlling the magnitude of the energization parameter, selecting the energization parameter based on the contact forces of the sequence of contact forces to prevent or reduce the incidence of steam pop. determining a size parameter of a lesion based on the force-time integral and the energization parameter, and/or instructions to terminate energization of the ablation head when the force-time integral reaches a predetermined value.

A force signal conditioning system can also be adapted to digitize the signal received from the force sensor and to provide the digitized signal to the central processor. For configurations utilizing a fiber optic force sensor, the force signal conditioning system can include a fiber optic interrogator operatively coupled with the fiber optic strain gauge and the central processor. The force signal conditioning system can also be adapted for the production of the sequence of contact force values (for example, to digitize the signal received from the force sensor and to provide the digitized signal to the central processor).

Methodologically, various embodiments of the invention include exerting the ablation head of the catheter against the target tissue, measuring a sequence of contact forces with the force sensor while the ablation head is exerted against the target tissue, the contact forces being in reaction to the exerting of the ablation head against the target tissue. The ablation head is then energized for a period of time while the sequence of contact forces is being measured. The sequence of contact forces measured with the force sensor over the period of time of energizing are then integrated to determine a force-time integral. In one embodiment, the method further involves determining an energization parameter delivered to the ablation head during the energizing of the ablation head, and determining the size parameter of the lesion based on the force-time integral and the energization parameter. The magnitude of the energization parameter can be selected based on the contact forces of the sequence of contact forces to prevent or reduce the incidence of steam pop.

BRIEF DESCRIPTION OF THE DRAWINGS

FIG. 1 depicts a schematic of a contact ablation system in an embodiment of the invention;

FIG. 2 depicts a test set up for determining the effects of constant or periodic force on lesion size in an embodiment of the invention;

FIG. 3 is an example time trace of a substantially constant sequence of forces generated by the test set up of FIG. 2;

DETAILED DESCRIPTION OF SELECTED EMBODIMENTS

Figure 4:
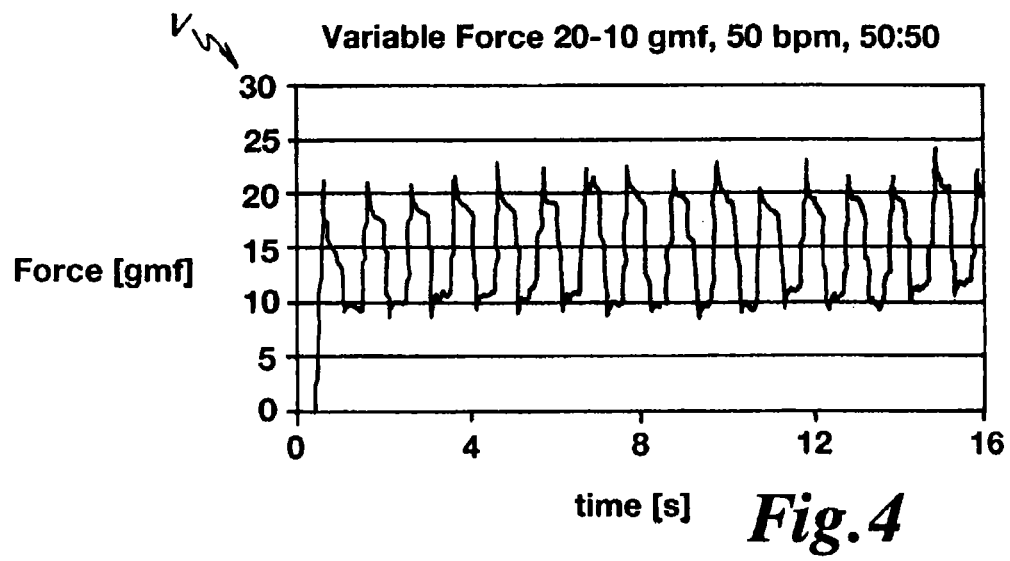
FIG. 4 is an example time trace of a variable sequence of forces generated by the test set up of FIG. 2.

Referring to FIG. 1, a contact ablation system 30 is depicted in an embodiment of the invention. The contact ablation system 30 includes a catheter 32 having a distal portion 34 comprising an ablation head 36 operatively coupled with a force sensor 38, the ablation head 36 arranged for contact with a target tissue 40. The catheter 32 is operatively coupled with a power source 42 that provides and measures the delivered energy to the ablation head 36. A measurement device 44 is also depicted, capable of sourcing the force sensor 38 and measuring an output signal from the force sensor 38.

In operation, the ablation head 36 is brought into contact with the target tissue 40 and energized to create a lesion 46 on and within the target tissue 40. The force sensor 38 is configured to generate an output from which a magnitude of the contact force can be inferred. Generally, the contact force is time-variant, particularly when the target tissue 40 is subject to motion (e.g., the wall of a beating heart). The energy flow (e.g., current or power) through the ablation head 36 can also be time variant, as the energy flow may depend on the contact resistance between the ablation head 36 and the target tissue 40, which in turn can vary with the contact force and the changing properties of the lesion 46 during ablation.

Various embodiments of the invention implement a force-time integral from which the size of the lesion 46 (volume, depth and/or area) can be predicted. A "force-time integral" is broadly defined herein as a measured quantity that involves the measurement of force over time. The force-time integral can be defined one of several ways, all involving the measurement of force over time. One example of a force-time integral is, of course, the numerical integration of the force over time (FOT):

$$FOT = \int F(t)dt \qquad \text{Eqn. (1)}$$

where F(t) is the contact force measured over time between a target tissue and a distal portion of an ablation head. The parameter t designates time, indicating that the contact force can be time variant.

The force-time integral can also be expressed a force-time product (FTP), given by $$FTP = \overline{F} \cdot \Delta t \qquad \text{Eqn. (2)}$$

where $\overline{F}$ is a representative value of F(t) over a time period $\Delta t$.

Another expression of a force-time integral comprises a force-energization over time (FEOT) integral or a force-energization-time product (FETP), given respectively as $$FEOT = \int F(t)E(t)dt \qquad \text{Eqn. (3)}$$

$$FETP = \overline{F} \cdot \overline{E} \cdot \Delta t \qquad \text{Eqn. (4)}$$

where E(t) is the measured energization indicative of the energy flow delivered to the ablation head (e.g., power or electrical current) and $\overline{E}$ is a representative value of the measured energization E(t) over the time period $\Delta t$ (for example a time-averaged energization value). The measured energization E(t) can also be time-variant, as noted above. The force-time-energization product (FETP) can include combinations of the above parameters, for example:

$$FETP = \overline{E} \int F(t)dt \qquad \text{Eqn. (5)}$$

$$FETP = \overline{F} \int E(t)dt \qquad \text{Eqn. (6)}$$

In another embodiment, a normalized force over time (NFOT) integration that is normalized with respect to the energization levels can also be implemented:

$$NFOT = \frac{\int F(t)E(t)dt}{\int E(t)dt} \cdot \Delta t \qquad \text{Eqn. (7)}$$

Such an approach may be useful for enhanced accuracy where only FOT or FTP calibrations are available.

It is further noted that with respect to the present invention the measurement of "force" per se is not necessary to infer or derive a force-time integral. Although force and strain or pressure may not be equivalent in other contexts, other parameters that have a relationship with force (e.g., strain, pressure) can be substituted for the force component of the force-time integral in the present invention and still reliably predict lesion size. Likewise, it is understood that other references to "force" herein (including, but not limited to, force sensor, force signal, force conversion, force set point, force interval, force values, force measurement, force level, force limits, contact force and reaction force) are intended to be broadly construed to include other parameters such as pressure and strain that have a relationship with force.

The various force-time integrals defined above can be useful in predicting the size of the lesion 38 that is created thereby. Methods and apparatuses for obtaining lesion size information and for utilizing this information in lesion creation and size prediction is discussed below.

Referring to FIG. 2, a test apparatus 50 was developed to determine the relationship between contact force-time integration and RF ablation lesion size in an embodiment of the invention. A motorized platform 52 was used to raise and lower a tissue specimen 54 (bovine muscle) under an irrigated ablation catheter 56 (2.3-mm diameter) fixed in space and having an ablation head 57 oriented substantially perpendicular to the tissue specimen 54. The ablation head 57 of the irrigated ablation catheter 56 was operatively coupled to a force sensor 58 (sensitivity<1 g, 64 Hz sampling rate). The force sensor 58 was incorporated as a feedback element into a programmable closed loop controller 60 to control a vertical displacement 62 of the motorized platform 52 to obtain desired contact force characteristics. The ablation head 57 was operatively coupled to a RF source 64, which was used to deliver unipolar RF energy to tissue specimen.

The set up was used to test three different contact conditions: constant CC, variable VC and intermittent IC. The constant contact condition CC simulated a constant contact force during the ablation period. The variable contact condition VC simulated continuous contact, but with forces varying in a periodic fashion to simulate the interaction of an ablation probe with a beating heart. The intermittent contact condition IC simulated periodic, non-continuous contact to simulate interaction of an ablation probe with a beating heart when contact is not continuous.

The experiment was conducted at constant power delivery levels of 20- and 40-watts. The time of energization was set at 60-sec., with irrigation of 17-cc/min of saline solution. The constant contact condition CC was tested at 20-grams force (gmf), where 1-gmf is equivalent to the weight of 1-gram of mass at standard gravity. The variable contact condition VC was tested with a periodically varying force between approximately 10-gmf minimum and 20-gmf maximum. The intermittent contact condition IC varied from 0-gmf minimum to 20-gmf maximum, with the 0-gmf condition maintained for a portion of the duty cycle. The V and I contact conditions were tested at simulated heartbeats of 50 and 100 beats per minute. Systolic-to-diastolic ratios of 50:50 and 30:70 were also simulated.

Figure 5:
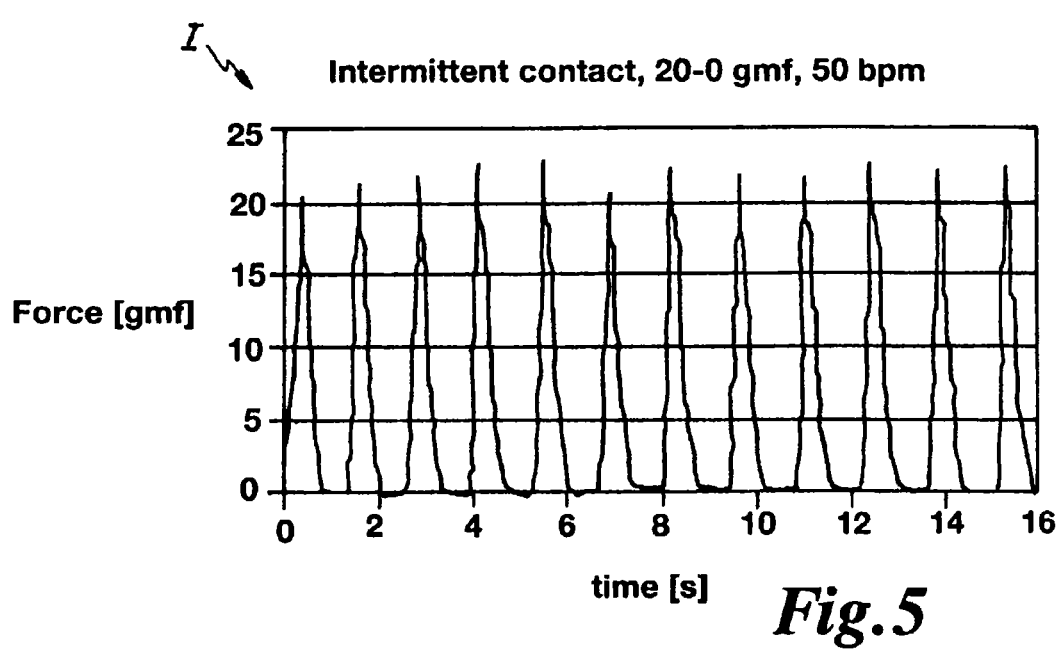
FIG. 5 is an example time trace of an intermittent sequence of forces generated by the test set up of FIG. 2.

Referring to FIGS. 3 through 5, example traces from the various contact conditions CC, VC and IC are presented in an embodiment of the invention. Fourteen lesions were created for the constant contact condition CC, 48 lesions for the variable contact condition VC and 35 lesions for the intermittent contact condition IC. The force-time integrals were highest for the constant contact condition CC, intermediate for the variable contact condition VC and lowest for the intermittent contact condition IC. Lesion depth and volume were greater for the constant contact condition CC than for the intermittent contact condition IC, and also greater for the variable contact condition VC than for the intermittent contact condition IC.

Figure 6:
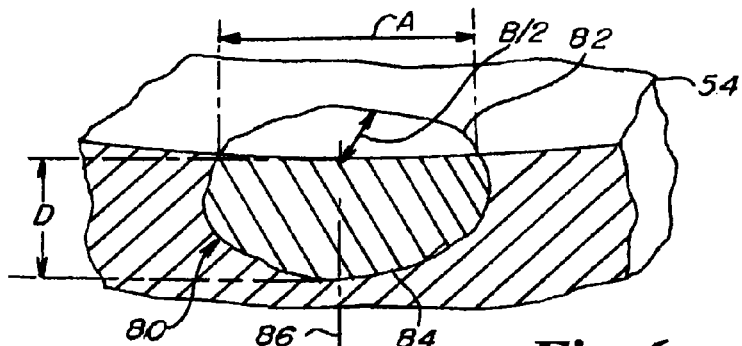
FIG. 6 is a sectional view of a test specimen after ablation in the test set up of FIG. 2.

Referring to FIG. 6, a depiction of the determination of the size (area, depth and volume) of a lesion 80 in the ablated tissue specimen 54 is presented in an embodiment of the invention. The lesion 80 is characterized as having a surface area 82 and a volume 84. The surface area 82 and volume 84 of the lesion 80 is determined by first measuring the diameter of the lesion, as determined by the border between discolored and non-discolored tissue. For lesion surfaces having an elliptical shape, a major diameter A and a minor diameter B is measured. The ablated tissue is then dissected through a central axis 86 of the lesion 80. Where the lesion surface is elliptical in shape, the dissection is made along either the major or minor diameter A or B. The depth D of the lesion 80 is measured on the dissected tissue specimen 54.

The surface area of the lesion may be determined by $$Area = \pi \cdot (A/2) \cdot (B/2) \qquad \text{Eqn. (8)}$$

The volume of the lesion may be estimated as half the volume of an ellipsoid:

$$Volume = 1/2 \cdot [(4/3) \cdot \pi \cdot (A/2) \cdot (B/2) \cdot D] \qquad \text{Eqn. (9)}$$
$$= \pi/6 \cdot A \cdot B \cdot D$$

Figure 7:
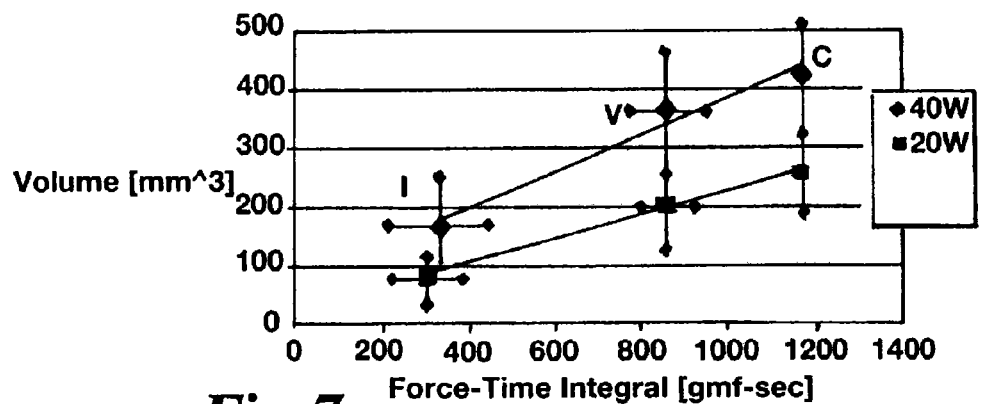
FIG. 7 is a graph of lesion volumes vs. force-time integral value at 20- and 40-watts in an embodiment of the invention.
Figure 8:
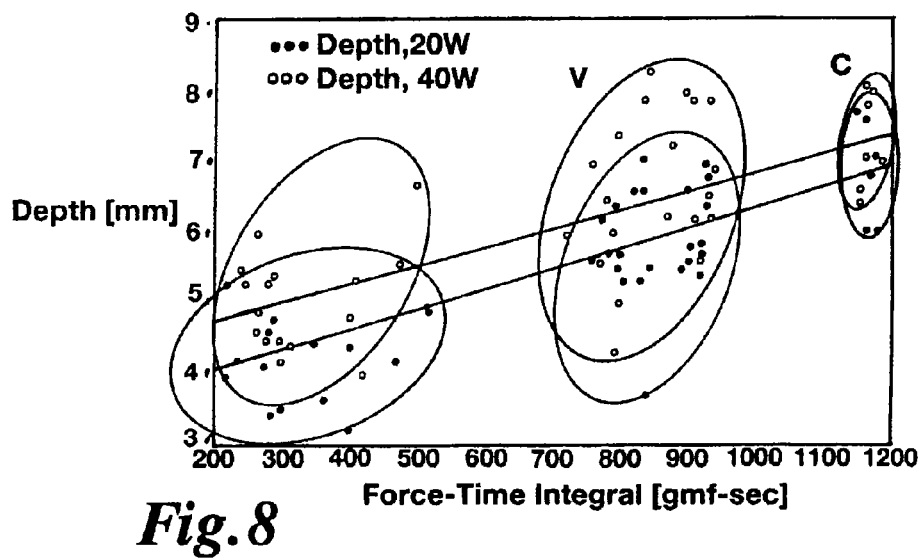
FIG. 8 is a graph of lesion depth vs. force-time integral value at 20- and 40-watts in an embodiment of the invention.
Figure 9:
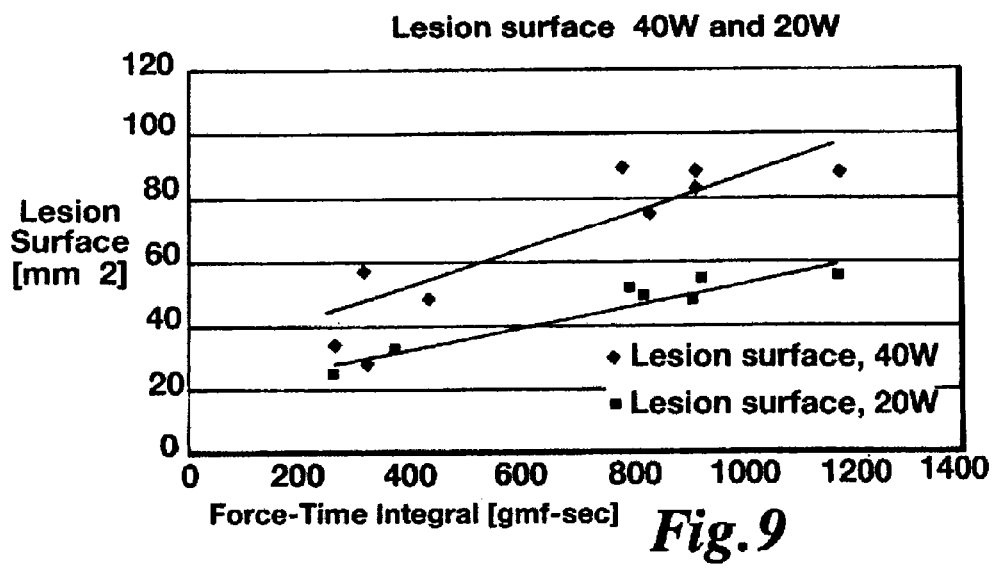
FIG. 9 is a graph of lesion area vs. force-time integral value at 20- and 40-watts in an embodiment of the invention.

Referring to FIGS. 7 through 9, the results of the integration of the force-time integrals versus lesion volume, depth and area acquired during the test are presented in an embodiment of the invention. A substantially linear correlation exists between the force-time integral and both the lesion volume and the lesion depth for both the 20- and 40-watt power delivery. No discernable relationship was found between lesion size and simulated heart rate or between lesion size and the systolic:diastolic ratio.

Accordingly, in one embodiment, a method of predicting lesion size in accordance with the invention is to establish the force-time integral (e.g. by integration or by the product of representative values as presented in Eqns. (1)-(7)) from the force signal over the time of energization of the ablation head and to infer a lesion size characteristic (e.g. depth, volume or area) from the integral via a linear correlation. This method can be made reliable to within a known uncertainty by acquiring a sufficient population of data points to enable statistical treatment of the data. It is noted that the estimation of area of the lesion (FIG. 9) can readily be converted to an equivalent diameter De:

$$De^2 = 4 \cdot A/\pi \qquad \text{Eqn. (10)}$$

Figure 10:
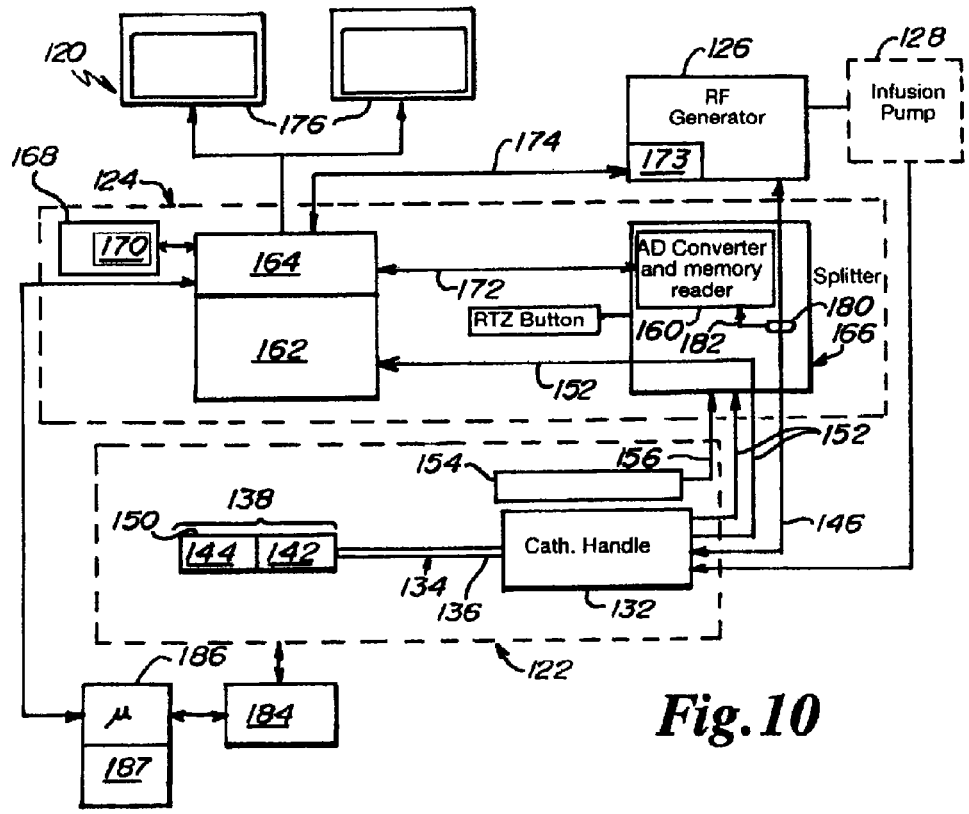
FIG. 10 depicts a schematic of a contact ablation system in an embodiment of the invention.

Referring to FIG. 10, a force sensing catheter-based contact ablation system 120 is depicted in an embodiment of the invention. The system 120 comprises a force sensing catheter assembly 122 operatively coupled to a data acquisition and processing unit or control system 124, a power source 126 and an infusion pump 128. The catheter assembly 122 may include a handle portion 132 operatively coupled with an elongate, flexible catheter 134 having a proximal portion 136 and a distal portion 138. The distal portion 138 includes a force sensor 142 operatively coupled with a contact ablation probe or ablation head 144 and adapted to output a signal in response to a contact force exerted on the ablation head 144. The ablation head 144 may comprise one or more electrodes operatively coupled to the power source 126 via a power cable 146. The ablation head 144 may also include one or more temperature sensors 150. Signals from the force sensor 142 and temperature sensor 150 (when present) may be routed to the control system 124 via instrumentation cabling 152. The catheter assembly 122 may also include a digital memory device 154 for storage of calibration parameters specific to the force sensor 142 and coupled to the control system 124 via a computer cable 156.

The control system 124 may include an analog-to-digital (A/D) converter 160, a force conversion module or force signal conditioning system 162 and a central controller or processor 164, all of which may be operatively coupled to an interface 166. The interface 166 may include connection for the various cabling 146, 152, 156 from the force sensing catheter assembly 122, and may also be operatively coupled to a tare or zero reset 68 for zeroing the force sensor 142. The central processor 164 may include or have access to a storage medium 168 that contains programming instructions 170 to be carried out by the central processor 164. The central processor 164 may also control and log data from the force signal conditioning system 162, and may also communicate with the A/D converter 160 via a communications cable 172, such as a RS-422 cable. In one embodiment, the power source may be equipped with an output controller 173 operatively coupled to the central processor 164 via a control line 174 for computer control of the power output. The central processor 164 may also provide real time information via one or more displays 176. A non-limiting example of the rate at which information is logged by the central processor 164 is approximately 60-Hz. A non-limiting example of the rate at which the displays are updated is approximately 10-Hz.

Force sensing can be achieved with strain sensors or distance/displacement sensors that sense the movement of a deformable body. Strain sensors include common resistive strain sensors, piezoelectric and piezoresistive elements and MEMS sensors. Distance sensors include capacitive, inductive and optical sensor technologies. For example, certain distance sensors utilize a single magnetic emitter opposite three pickup coils to measure the local intensity changes at each coil and therefore the strain on the body.

Generally, the force signal conditioning system 162 comprises equipment for driving or sourcing the sensing element or elements of the force sensor 142 and/or digitizing or monitoring an output of the force sensor 142. For example, if the force sensor 142 implements foil-type strain gauges in a Wheatstone bridge configuration, the force signal conditioning system 162 may include an excitation source, a signal conditioner for conditioning and amplification of the output of the Wheatstone bridge, and an A/D converter (not depicted). The force signal conditioning system 162 may also include firmware that converts the digitized output into engineering units (e.g. newtons, pounds-force or grams-force). Alternatively, the digital signal may be converted to engineering units by the central processor 164.

In one embodiment, the force sensor 142 comprises one or more fiber optic strain elements, such as fiber Bragg grating(s) or Fabry-Perot resonator(s). In this embodiment, the instrumentation cabling 152 includes fiber optic cables and the force signal conditioning system 162 comprises a fiber optic interrogator, such as the MicronOptics model is SM125 (for fiber Bragg grating interrogation) and the FISO model FCM (for Fabry-Perot interrogation).

A current detector 180 may be operatively coupled with the power cable 146 for detection of the electrical current flowing to the ablation head 144. The current detector 180 may be operatively coupled to the A/D converter 160 for processing by the central processor 164. In one embodiment, the current detector 180 comprises a conductive coil surrounding the power cable 146 which produces an output signal 182 proportional to the magnetic field generated by the AC current passing through the power cable 146.

In one embodiment, a robotic manipulator 184 can be operatively coupled to the force sensing catheter assembly 122. The robotic manipulator 184 may be operatively coupled to a local microprocessor controller 186. The local microprocessor controller 186 can be controlled by a user from a local interface 187, and/or from the central processor 164. Alternatively, control of the robotic manipulator 184 may be provided by the central processor 164 directly, which may eliminate the need for a separate microprocessor controller and attendant interface.

Functionally, the robotic manipulator 184 can be made to respond to the commands of the local microprocessor controller 186 to control the movement of the catheter 134 and the magnitude of any subsequent reaction force exerted on the ablation head 144. The movement may be the controlled parameter in a closed loop control scheme, and the force measured by the force sensor 142 the feedback measurement. A desired force set point or desired force interval set point may be provided to the local microprocessor controller 186 by an operator via the local interface 187 or via the central processor 164.

Optionally, the desired force or force interval may be calculated from a determinative parameter provided by the operator or by the control system 124. For example, consider an application where a lesion size having a volume of 300 cubic millimeters is desired at an energization of 30 Watts. From FIG. 7, a force time integral of approximately 1000 gmf-sec provides the determinative parameter from which the desired force or force interval is derived. The robotic manipulator 184 can then be activated to apply the desired force or force interval that, in conjunction with the time of energization of the ablation head 144, produces the force-time integral. The force applied by the robotic manipulator 184 may be controlled by the local microprocessor controller 186 at the desired force or within the desired force integral, while the force values and energization time are monitored by the control system 124 until the stipulated force-time integral is achieved. The process may be terminated by the control system 124 by shutting off the power to the ablation head 144.

Figure 10A:
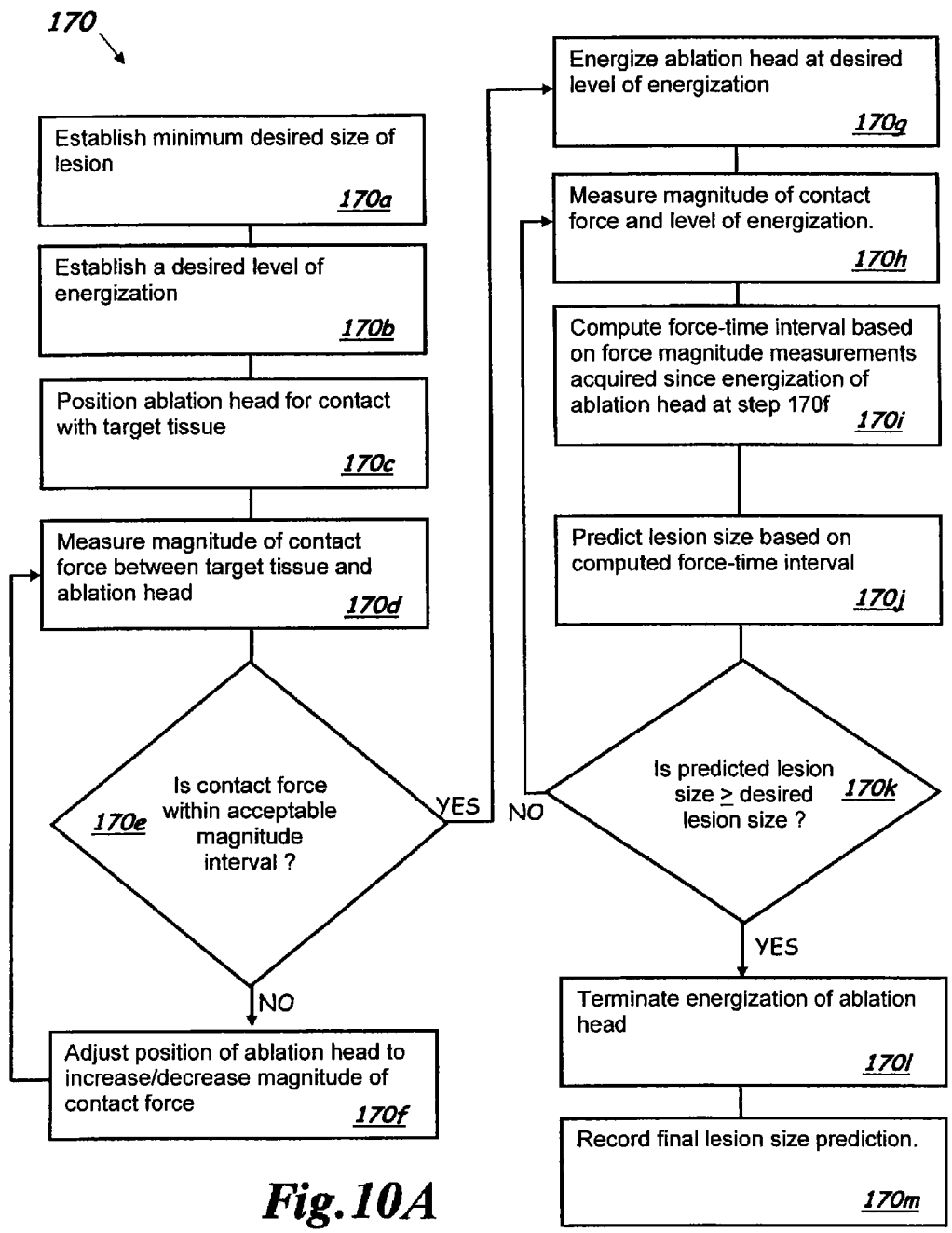
FIG. 10A depicts a schematic of programming instructions in an embodiment of the invention.

Referring to FIG. 10A, an example of the programming instructions 170 is depicted in an embodiment of the invention. In this embodiment, a minimum desired size and desired energization are initially established at steps 170*a* and 170*b*, respectively, for example by user input. The ablation head is then brought into contact with the target tissue (step 170*c*), for example by sending commands to the robotic manipulator 184. The magnitude of the contact force between the target tissue and the ablation head is measured at 170*d* and compared with a predetermined acceptable magnitude interval at step 170*e* (e.g., the desired force interval 198 of FIG. 11). If the contact force is not within an acceptable magnitude interval, the position of the ablation head is adjusted to increase or decrease the magnitude of the contact force (step 170*o* and the magnitude of contact force re-measured by repeating step 170*d*. The loop of steps 170*f*, 170*d* and 170*e* and is repeated until the measured contact force between the target tissue and the ablation head fall within the acceptable magnitude interval at step 170*e*. The programming instructions 170 then instruct the central processor 164 to energize the ablation head 144, for example by control of the RF generator 126 via the output controller 173, at a desired level of energization at step 170*g* (e.g., establishing a set point for electrical current or power).

Once the ablation head is energized, the embodiment depicted at FIG. 10A then goes into a loop comprising steps 170*h*, 170*i*, 170*j* and 170*k*. Within the loop, the magnitude of the contact force and the level of energization is measured at step 170*h*, and a force-time integral (e.g., any one of Eqns. (1) through (7)) is then computed based on the force magnitude measurement acquired at step 170*h* since energization of the ablation head at step 170*f*. A prediction of the lesion size based on the force-time interval computed at step 170*i* is then made (step 170*j*), and a comparison with the desired lesion size made at step 170*k*. If the predicted lesion size is greater than or equal to the desired lesion size, the loop at steps 170*h* through 170*k* is terminated; otherwise, steps 170*h*, 170*i*, 170*j* and 170*k* are repeated. Once the loop at steps 170*h* through 170*k* is terminated, the energization of the ablation head is also terminated (step 170*l*) and the final lesion size prediction is recorded (step 170*m*) in computer memory.

Figure 11:
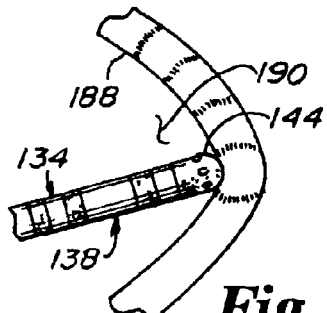
FIG. 11 is an enlarged partial sectional view of an atrium wall during lesion generation in an embodiment of the invention.

Referring to FIG. 11, operation of the entry of the catheter 134 into a patient can be made via a vein in the neck or groin of a patient and route the catheter 134 through the vein to the heart 188 of the patient. The distal portion 138 of the catheter 134 can be caused to enter an atrium 190 of the heart 188 and the ablation head 144 brought into contact with the wall of the atrium 190. Adequate contact between the ablation head 144 and the wall of the atrium 190 causes the control system 124 to register a meaningful force measurement originating from the force sensor 142 and posting the result on the display 176 in real time. The use of a plurality of displays enables the force information to be presented at several locations, for example in the operating room for the benefit of the operator and in a control room (often separate from the operating room) for the benefit of an assistant.

The operator then adjusts the position of the distal portion 138 of the catheter 134 until a desired level of force is posted on the display 176. Upon reaching the desired force level, the operator may then energize the ablation head 144 for a desired time period, creating a lesion on the atrium wall. The operator may repeat the process at other locations to create a desired pattern of lesions on the atrium wall, such as depicted in FIG. 11.

Figure 12:
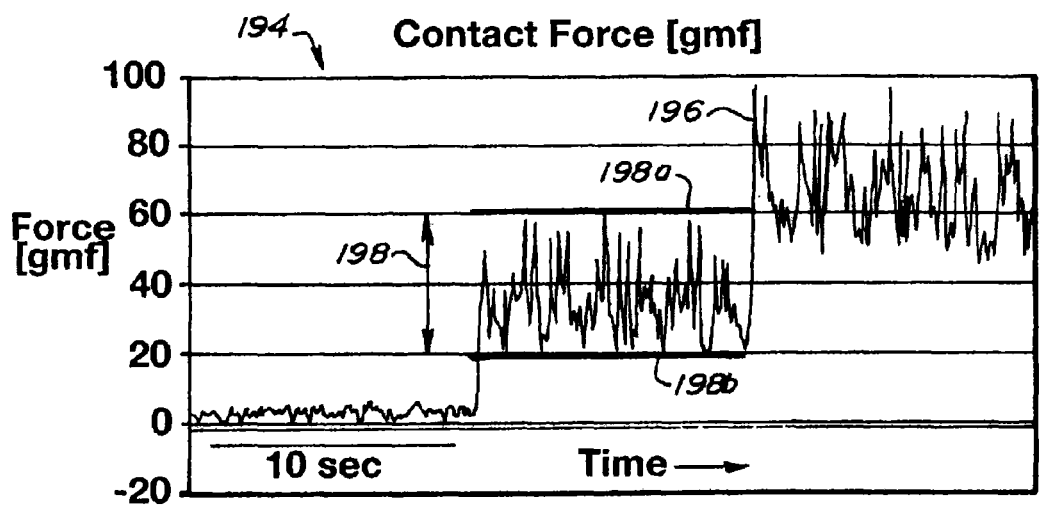
FIG. 12 is a time trace of contact forces generated in vivo by a force generating probe in an embodiment of the invention.

Referring to FIG. 12, a time trace 194 of forces 196 registered by the control system 124 are depicted in an embodiment of the invention, with an example and non-limiting indication of a desired force interval 198. The depiction of the time trace 194 may be displayed real time on the displays 176. The forces 196 will typically be of an undulating nature due to the systolic and diastolic movement of the heart 188. The data presented on the displays 176 may be in the form of an instantaneous numeric value, a time-averaged numeric value of a number of data points, a time trace of the time averaged numeric values, or some combination thereof. The presentation of the data on the displays 176 may be tailored to inform the operator when the forces 196 are within the desired force interval 198, such as by identification of upper and lower force limits 198a and 198b on the time trace 194 or by presenting an indication when a time-averaged value has remained within a desired interval for a period of time.

The control system 124 can be adapted to integrate the force-time parameters while acquiring and displaying data. The central processor 164 may be configured to start the integration of the force-time integral when the operator initiates power to the ablation head 144 and to shut off the power from the power source 126 when the force-time integral reaches a predetermined value. In one embodiment, the predetermined value may be based on the area or zone of the heart to be ablated, recognizing that not all tissues of the heart respond the same to contact ablation. The predetermined value may also or instead be based on the lesion size desired by the operator, using a correlation such as provided in FIGS. 7 through 9 that establishes the force-time integration value corresponding to the desired lesion size. Such dynamic computation of the force-time integral may provide more reliable results. All the operator need do is initiate the power; the central processor 164 determines when to shut off the power based on the force-time integral.

In one embodiment of the invention, the central processor 164 may be programmed to control an energization parameter (e.g., power or current) delivered to the ablation head 144 based on the force sensed by the force sensor 142. The central processor 164 can monitor the force resolved by the force signal conditioning system 162 and determine a desired energization magnitude that corresponds to the resolved force. The central processor 164 may then control the output (e.g., amperes or watts) of the power source 126 using the power controller 173.

The control of the power source 126 may be open loop or closed loop. In an open loop configuration, the power source 126 may be calibrated so that the setting of the power source 126 (e.g., voltage or current) produces a known output (e.g., current or power) to within an acceptable uncertainty. In a closed loop configuration, the output signal 182 of the current sensor 180 may be utilized to provide the feedback parameter. The output signal 182 of the current sensor 180 may be conditioned to temper the unsteadiness of the current caused, for example, by intermittent contact. The determination of power or current level desired for a nominal contact force may be accomplished by a mathematical function or a lookup table stored in the memory of the central processor 164. In one embodiment, the controlled current level may be greater than 0.2 amps. In another embodiment, energy delivery may be tailored so that the current level does not exceed 2 amps.

Functionally, controlling the magnitude of the energization parameter based on the contact force can prevent or reduce the incidence of steam pop. The force vs. energization relationship may be tailored to this purpose. The power prescribed for a given force could be chosen so that the chances of steam pop is reduced, and/or so that any steam pop that does occur is not severe enough to cause cardiac perforations.

It is further noted that time variation in the magnitude of the energization parameter doesn't preclude the use of the force-time integration technique. While the calibrations of FIGS. 7 through 9 were made at constant power levels of 20- and 40-watts, the linear relationship between the force-time integral variable and the lesion size suggests that linear interpolation or extrapolation between the two functions should be reliable. Therefore, calibration data such as provided in FIGS. 7 and 8 can be manipulated to provide lesion size as a function of both force-time integral and the ablation power.

It is noted that while the data presented herein (i.e. lesion size vs. force-time integral and power) can form the basis of linear interpolations, the invention is not limited to linear interpolation of these parameters. For example, additional functions at other energization parameter levels (e.g., 25-, 30- and/or 35-watts) could provide the basis of a higher order interpolation between energization parameter levels.

In an alternative embodiment, the control system 124 may instead measure the energization parameter of the power source 126 to establish the desired force level for the operator to target based thereupon. The desired, power-adjusted force level may be displayed on the displays(s) 176 numerically, as an interval on a time trace, or both.

In another embodiment, estimates of the lesion size may be based on the time spent in a given contact condition (CC, VC or IC) For example, a force measurement could be made once during the contact condition and assumed constant throughout the contact interval. Determination of the contact time could be made another way (e.g., with an EKG) and multiplied by the force to arrive at a force-time integral value of low resolution. Such a method would require only a limited number of measurements and lower the time resolution requirements of the force measurements.

Figure 13:
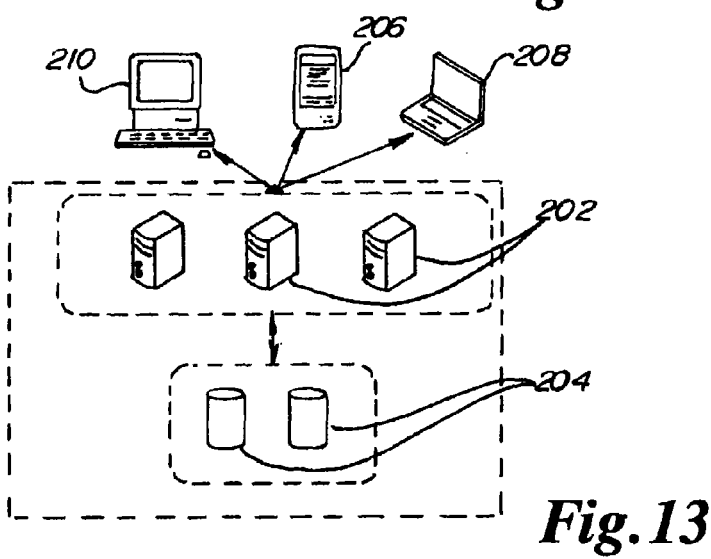
FIG. 13 depicts a schematic view of a computer system in an embodiment of the invention.

Referring to FIG. 13, the central processor 164 in one embodiment of the catheter-based contact ablation system 120 may connect to a Hospital Information System (HIS) 200. The HIS 200 may contain several application servers 202 and database system 204 in which medical records and medical operations data is stored and executed. Thus, in this embodiment, the central processor 164 may communicate information relating to the characterization and visualization of the lesions in the ablation procedure to the HIS 200 in order to make the information part of the medical record history. In various embodiments, the characterization and visualization of lesion information may be later viewed utilizing a variety of computing devices such as handheld portable devices 206 laptop or nettop computers 208 and desktop workstations 210. A person having skill in the art will recognize that the characterization and visualization of lesion information may be viewed on any device utilizing viewing functions either implemented in hardware or computer executable software.

Figure 14:
FIG. 14 depicts a 3D virtual model of an organ in an embodiment of the invention.
Figure 15:
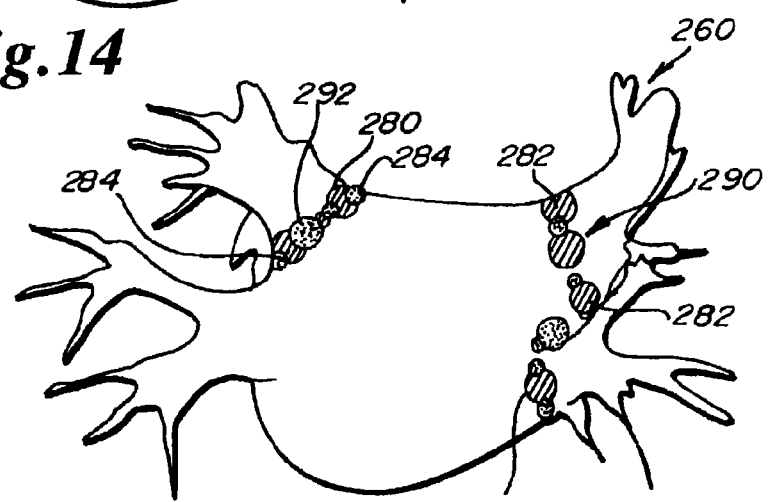
FIG. 15 depicts a 3D virtual model of an organ with visual depictions of lesions in an embodiment of the invention.
Figure 16:
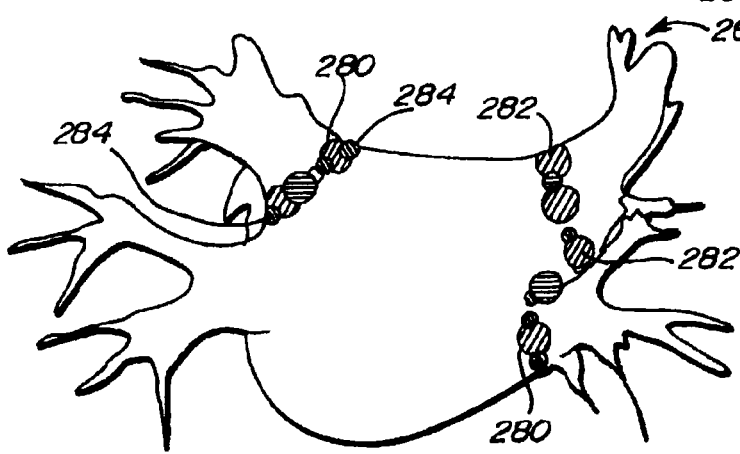
FIG. 16 depicts a 3D virtual model of an organ with alternate visual depictions of lesions in an embodiment of the invention.
Figure 17:
FIG. 17 depicts a 3D virtual model of an organ with alternate visual depictions of lesions in an embodiment of the invention.
Figure 18:
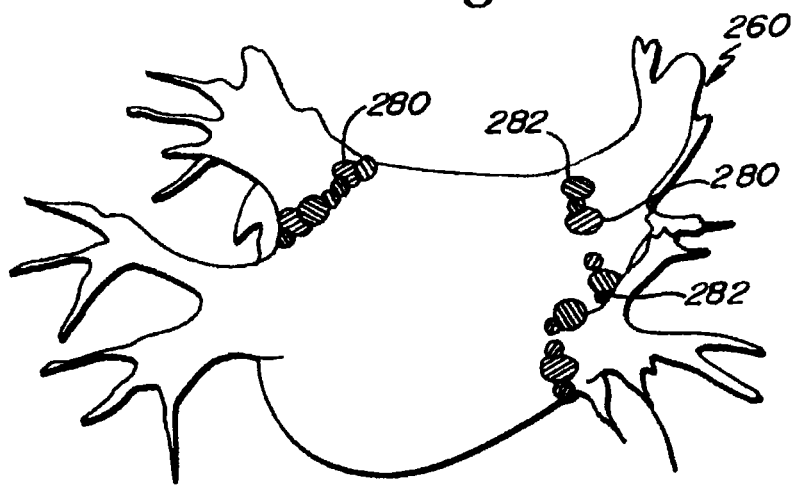
FIG. 18 depicts a 3D virtual model of an organ with alternate visual depictions of lesions in an embodiment of the invention.

Referring to FIG. 14, a 3D virtual model of an organ is presented according to one embodiment of the invention. In these embodiments, the 3D virtual model is a virtual model of a patient's heart 260. As mentioned earlier a high-resolution 3D model of the heart 260 may be created utilizing a variety of procedures including Magnetic Resonance Imaging (MRI) and Computed Tomography (CT). The MRI or CT scan in then mapped or fused to a system of geographic coordinates. Thus, following the mapping procedure, the operator has a high resolution 3D virtual model 260 of a patient's heart. The 3D virtual model 260 may be communicated and stored in the HIS 200 and become part of the patient's medical record.

In certain embodiments the 3D virtual model 260 is used in conjunction with location-aware force sensing catheters to generate location-sensitive characterizations and visualization of lesions. In various embodiments force sensing catheters utilize magnetic sensors or electrical sensors to estimate the position of the catheter within the heart cavity. For example, electrode patches placed on the patient may interface with a force sensing EP catheter to track location of the catheter within the patient's heart. This position may then be mapped to the 3D virtual model 260 to provide real-time or near real-time catheter position information to the operator.

Referring to FIGS. 15 through 18 the characterization and visualization of lesions according to various embodiments of the invention are presented. In various embodiments, the operator, during an ablation procedure will guide the force sensing catheter 134 to a location of interest. The distal portion 138 of the catheter 134 may be caused to enter an atrium of the heart. The contact ablation probe 144 may be brought into contact with the wall of the atrium, causing the data acquisition and processing unit 124 to register a meaningful force measurement originating from the force sensor 142 and displayed on the display 176 in real time. The operator then adjusts the position of the distal portion 138 of the catheter 134 until a desired level of force is posted on the display 176. Upon reaching the desired force level, the operator may then energize the contact ablation probe 144 for a desired time period, creating a lesion on the atrium wall. The operator may repeat the process at other locations to create a desired pattern of lesions on the atrium wall. In various embodiments, the level of force, temperature, and time period of applied energy is recorded by the data acquisition and processing unit 124.

While the data acquisition and processing unit 124 is acquiring and displaying data, the system may also be compiling, characterizing and producing visualization information. The central processor 164 may be configured to compile, characterize and visualize lesion information during each iteration of an operator's initiation of power to the contact ablation probe 144. The central processor 164 may then overlay the computed lesion information on the 3D virtual model 260.

In various embodiments data acquisition and processing unit 124 characterizes and visualizes lesions generated during an ablation procedure. In various embodiments the data acquisition and processing unit 124 may utilize information related to metrics such as contact, touch force, power, temperature, electrical impedance, force-time integral or any combination thereof to characterize and visualize lesion information. Further, the data acquisition and processing unit 124 can estimate the area, depth and volume of affected tissue at each ablation site and apply a different visualization depicting these estimates.

In some embodiments the data acquisition and processing unit 124 utilizes magnitudes to further characterize lesion coverage. For instance, in various embodiments, the data acquisition and processing unit 124 overlays the estimated lesion characteristics of on the 3D virtual model 260 utilizing a high magnitude 280, a medium magnitude 282 and a low magnitude 284 of a metric such as force, time, temperature, power, electrical impedance or force-time integral. Specifically, one embodiment characterizes lesions created utilizing high force (over 20 g), medium force (between 10 g and 20 g) and low force (below 10 g) as the high, medium and low magnitudes 280, 282, 284, respectively. In various embodiments, each magnitude level has a different visualization, such as varying area, color, stroke, opacity or fill pattern to differentiate between the lesions at each threshold level, at each location. Further, the visualization may represent each lesion by its own defined area 290 or visual effect 292 or may merge the borders of each lesion location to provide views of overall coverage and magnitude level as depicted in FIGS. 5 and 6. In other embodiments the visualization may represent each metric magnitude level using a separate visual effect. For instance, in certain embodiments the magnitude of force-time integral may be represented by area while the magnitude of temperature is represented by a color. One having skill in the art will appreciate that the differentiation of metrics into magnitudes is not limited by the present disclosure. Thus, in certain embodiments, metrics are organized into fewer than three magnitudes while in other embodiments metrics are organized into at least three magnitudes. Further, one having skill in the art will appreciate that in various embodiments the delineation of metrics into magnitudes may be altered utilizing a system setup or preferences operation that allows for the alteration of metric delineation.

In various embodiments, the visualization may be altered to conform to results of further pathological analysis of lesions at each magnitude level. For instance, in certain embodiments the visualizations of high magnitude 280 and medium magnitude 282 may be ovals having varying aspect ratios (ratios of major diameter to minor diameter) to better reflect the physical manifestation of the lesion in the patient's heart tissue. In this way, the operator is provided with an estimate of lesion area and coverage in a patient's heart. Additionally, in various embodiments, the data acquisition and processing unit 124 may provide the operator a visual history of the procedure such as a time-lapse visualization of the procedure for making decisions regarding further lesion sites or for implications on patient care.

In one embodiment the force-time integral is utilized to overlay a visualization, such as a dot, of the predicted lesion size. In this embodiment, the magnitude of force or the magnitude of time proportionally affects the diameter of the visualized dot. In another embodiment, the force, time and power integral is utilized to predict the lesion size. In various embodiments a color code is used to mark the estimated lesion size. For example, yellow for a small lesion and red for a large lesion. In yet another embodiment, the diameter of a visualized dot represents the estimated lesion area and the color of the visualized dot represents the estimated lesion depth.

Figure 19:
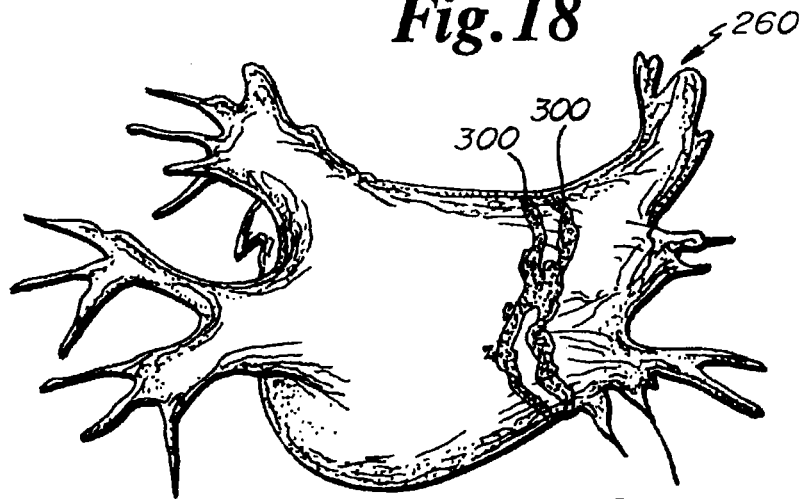
FIG. 19 depicts a 3D virtual model of an organ with visual depictions of lesions created by contact density mapping in an embodiment of the invention.
Figure 20:
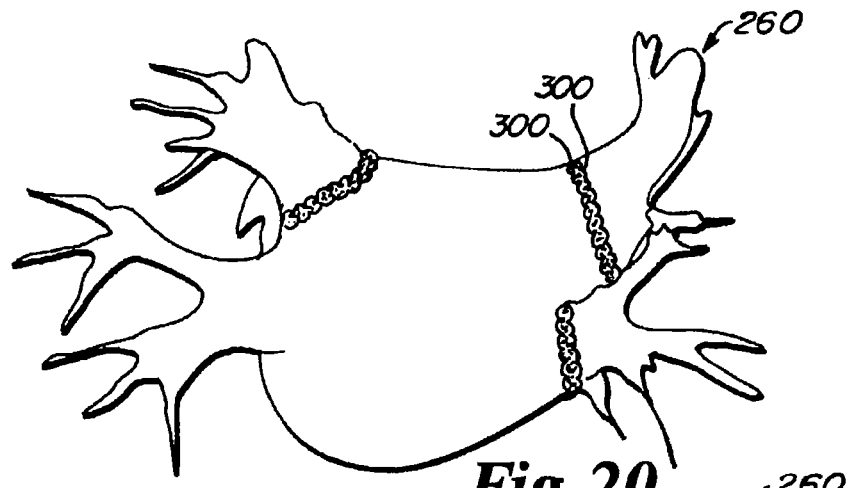
FIG. 20 depicts an alternate 3D virtual model of an organ with visual depictions of lesions created by contact density mapping in an embodiment of the invention.

Referring to FIGS. 19 and 20 examples of visualization utilizing contact information provided by the force sensing catheter to map lesions of heart tissue are presented according to one embodiment of the invention. In various embodiments, the data acquisition and processing unit 124 overlays a visualization of each contact point 300 of the force sensing catheter on the 3D virtual model 260. In one embodiment each visualized contact point represents approximately 1 second of contact during an ablation procedure. In another embodiment, visualizations, such as dots, are overlaid at a rate which depends on the force-time integral. In a related embodiment, visualized dots are overlaid at a rate depending on the force-time and power. Thus, in these embodiments areas of the 3D virtual model will have a higher density of visualized dots where lesion size is believed to be more extended. In certain embodiments this visualized dot density will be representative of how much energy was delivered to a certain area of the organ. In this way, the data acquisition and processing unit 124 can provide a graphical representation of organ tissues with highest duration and coverage of contact during ablation which may affect operator decisions on lesion location and the ablation procedure.

Figure 21:
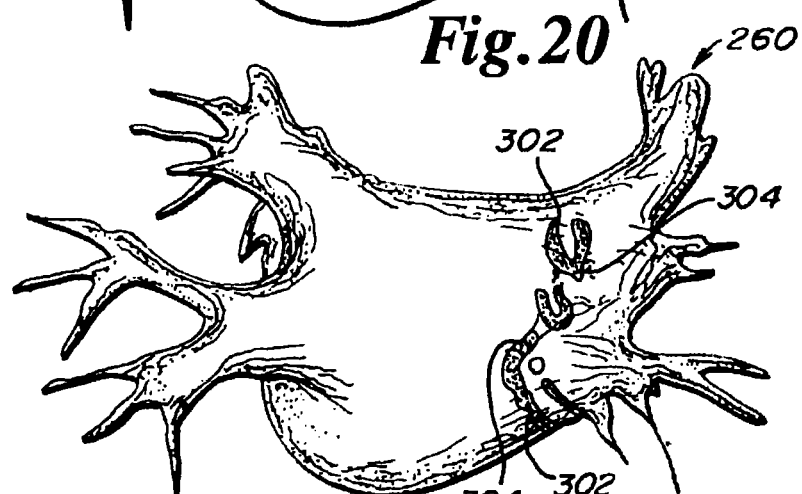
FIG. 21 depicts a 3D virtual model of an organ with visual depictions of lesions created by force contact density mapping in an embodiment of the invention.
Figure 22:
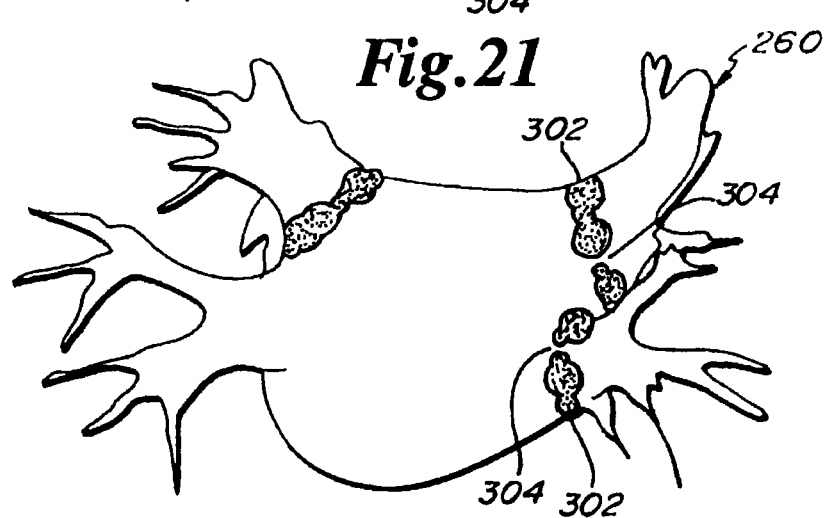
FIG. 22 depicts an alternate 3D virtual model of an organ with visual depictions of lesions created by force contact density mapping in an embodiment of the invention.

Referring to FIGS. 21 and 22, the visualization of force combined with contact to map lesions of heart tissue are presented according to one embodiment of the invention. In various embodiments, the data acquisition and processing unit 124 overlays a visualization of each contact point combined with force 302 of the force sensing catheter on the 3D virtual model 260. In one embodiment each visualized contact point exhibits a varying diameter based on the amount of force utilized in the contact. For example, a contact point made using low force will have a visualization with a small diameter whereas a contact point made using a large amount of force will have a large diameter. In other embodiments, the diameter may vary with some other metric, such as the force-time integral. In this way, the data acquisition and processing unit 124 can provide an additional graphical representation of heart tissues with highest duration, force and coverage of contact during ablation.

In another embodiment, the diameter of the lesion may be representative of the actual area of the predicted lesion size, as predicted by the force-time integration technique. The area may be converted to an equivalent diameter which can be scaled to give a proportionally true estimate of the lesion diameter on the model.

In various embodiments, power may be combined with contact and force to map lesions of heart tissues on a 3D virtual model 260. In this embodiment, the data acquisition and processing unit 124 overlays a visualization of each contact point combined with force and power of the force sensing catheter on the 3D virtual model 260. In one embodiment each visualized contact point exhibits a varying diameter based on the amount of force and power utilized in the contact. In one embodiment, the visualized contact point may depict a varying amount of ovality based on the amount of power utilized in the contact. For example, a contact point made using low force and power will have a visualization with a small area and mainly circular in shape whereas a contact point made using a large amount of force and power will have a large diameter and be significantly oval. In other embodiments, additional visual effects are used to represent each metric used to estimate the lesion. For example, the magnitude of time may be represented by a fill pattern, power by color and force by opacity. In this way, the data acquisition and processing unit 124 can provide an additional graphical representation of heart tissues with highest duration, force, power and coverage of contact during ablation.

In still another embodiment, a first metric may be represented by a varying diameter while a second metric is represented by a varying color or darkness. For example, the magnitude of the force-time integral may be represented by the diameter of the contact point, as depicted in FIG. 11, while the power level is represented by the color or darkness of the contact point (e.g., light gray for low power, medium gray for medium power and black for high power). Thus, in various embodiments each metric utilized in the visualization of a lesion will be represented by a different visual effect, giving the operator an indication of the magnitude of the metric at that location.

In various embodiments, the visualization of the force-contact density combination or the force-power-contact density combination can provide the operator with a reliable determination of tissue damage such as tissue perforation 304. In these embodiments, the combination of force or force and power at a contact point allows the data acquisition and processing unit 124 to characterize tissue areas subject to a high likelihood tissue damage such as perforation. In this way, these embodiments provide the operator with early indications of possible procedure complications and allow for remedial actions if necessary. Further, the use of force or force and power allows for predictability of tissue damage not present when utilizing only catheter contact information. Thus, the visualization of force or force and power to determine tissue damage is helpful in discerning possible physical manifestations as a result of ablation procedures.

In other embodiments, the visualization of force combined with contact density or force and power combined with contact density may provide the operator with estimates of the location of edemas or tissues resistant to the ablation procedure. In these embodiments the data acquisition and processing unit 124 may determine that contact, force or power was insufficient in lesion creation and may identify the point as an area of possible edema or resistance. In various embodiments these areas may be visualized utilizing a different visual effect such as varying color, stroke or gradient.

In still other embodiments, the visualization of force combined with contact density or force and power combined with contact density may provide the operator with estimates of the location of gaps in the isolation line. In these embodiments the data acquisition and processing unit 124 may determine that contact, force or power was insufficient in electrical isolation and may identify the point as an area of a possible isolation gap. In various embodiments these areas may be visualized utilizing a different visual effect such as varying color, stroke or gradient.

Figure 23:
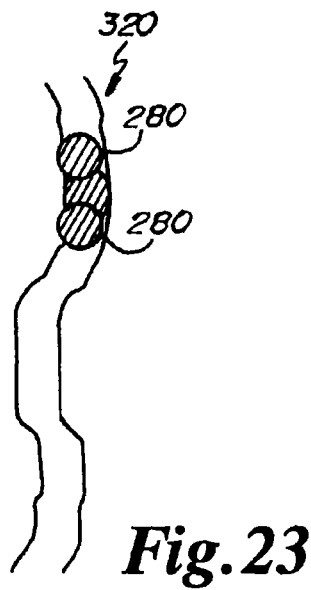
FIG. 23 is a cross sectional view of an organ wall with visual depictions of lesions in an embodiment of the invention.

Referring to FIG. 23 a cross-section 320 of the 3D virtual model 160 is presented. In various embodiments, the 3D virtual model 160 may be cross-sectioned to examine different views of the characterized and visualized lesion, such as lesion depth and cross-section based on an assumed shape of the lesion volume. For example, the volume of the lesion may be assumed to be that of a hemisphere or half-ellipsoid. Given a predicted lesion depth and volume, the boundary of the lesion cross-section can be estimated. Thus, an operator may view the estimated depth of a visualized lesion by taking a cross-section view of the 3D virtual model 160.

In a related embodiment, the data acquisition and processing unit 124 may provide estimates of transmural lesion. Thus, a visualization of the probability of transmural lesion may be represented using an additional visual effect. For example, a visual effect such as color, hue or transparency may be used to present a visualization of the magnitude of the probability of transmural lesion at a location while the diameter of the contact point represents the magnitude of the force-time integral.

Figure 24:
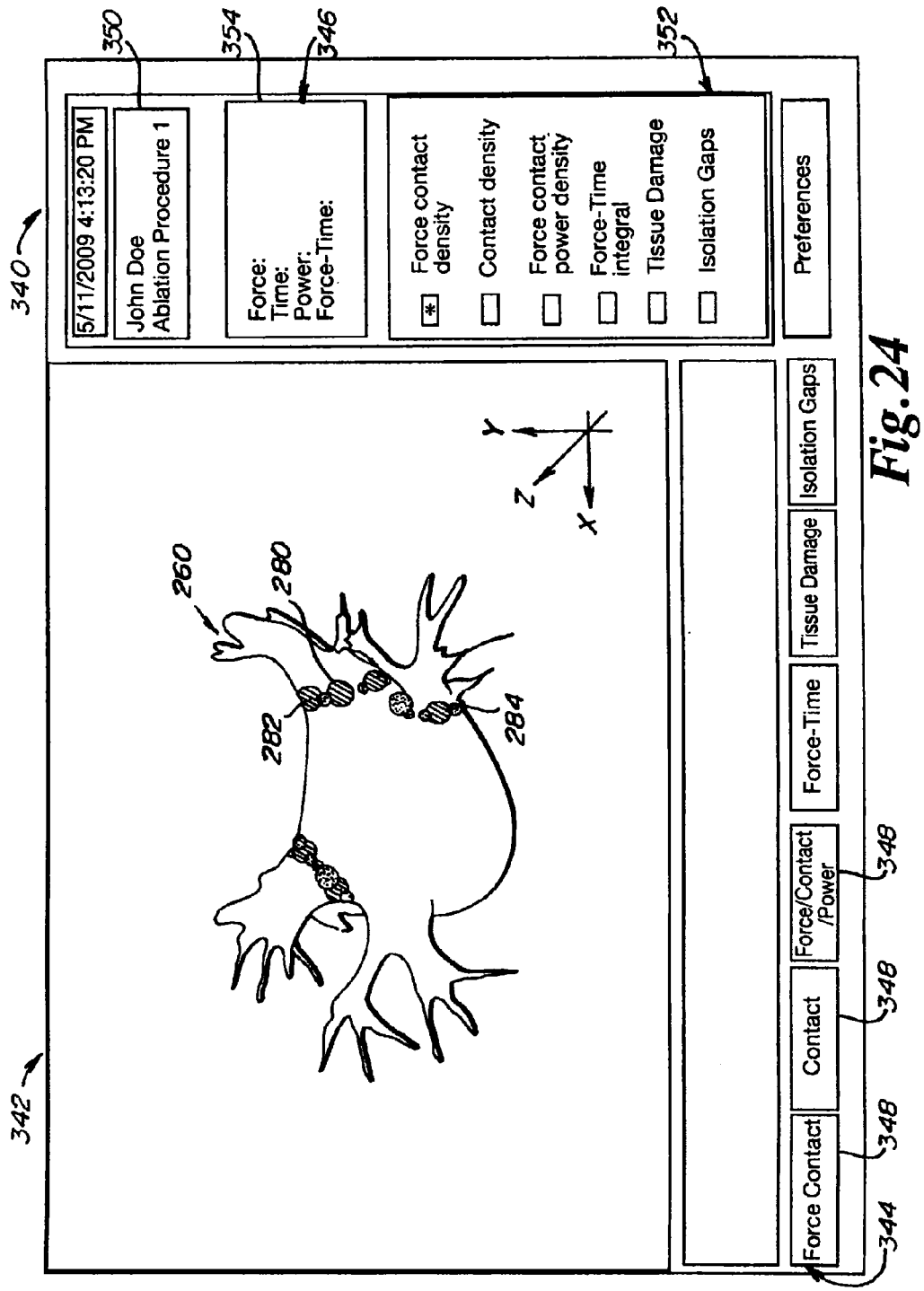
FIG. 24 depicts a computer system interface for displaying the visual depictions of lesions in an embodiment of the invention.

Referring to FIG. 24 a visualization user interface 340 according to one embodiment is presented. The visualization user interface 340 may have a 3D model display pane 342, a control pane 344 and an information pane 346. The 3D model display pane may be manipulated using a mouse, keyboard, joystick or similar user interaction device. In this way the operator can manipulate the 3D virtual model in the X, Y and Z planes in order to visualize lesions in all areas of the heart. Further, the 3D model display pane may be able to display cross-sectional views of heart tissue by selecting a slice operation, or zooming into the tissue utilizing zoom controls. The control pane 344 may have several option menus or buttons 348 in which the operator may select different visualization options as described herein. The control pane 346 is configurable and supports a modification in the placement, size and number of operational controls. The information pane 346 may provide the operator with information related to the patient 350 the selected visualization 352. Further, the information pane may provide the operator with information related to each visualization of a lesion 354 when the operator utilizes a cursor to highlight areas of the 3D virtual map with lesion visualizations. The information pane 346 is configurable and supports a modification in placement, size and content of information presented.

Figure 25:
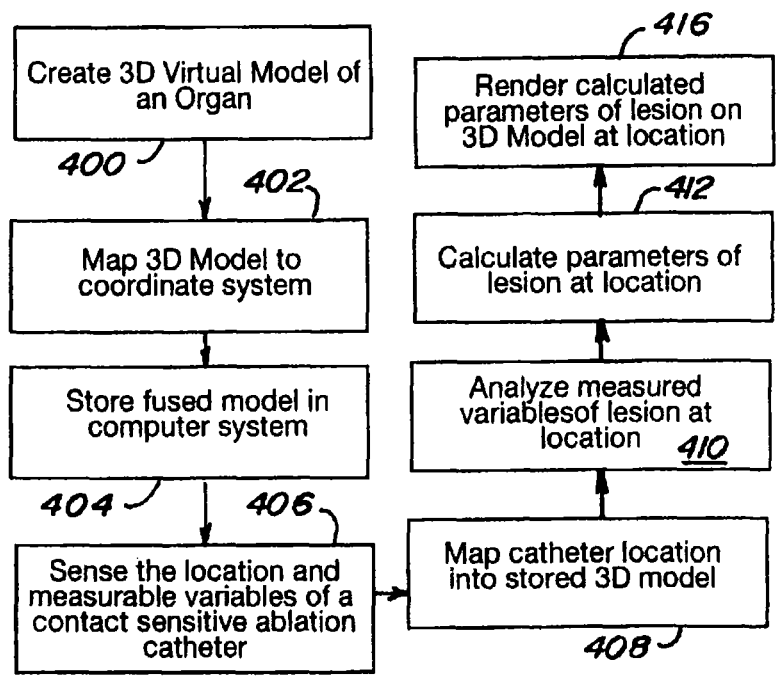
FIG. 25 depicts a flow chart of the steps for generating and displaying lesions on a 3D model of an organ according to one embodiment of the invention.
Figure 26:
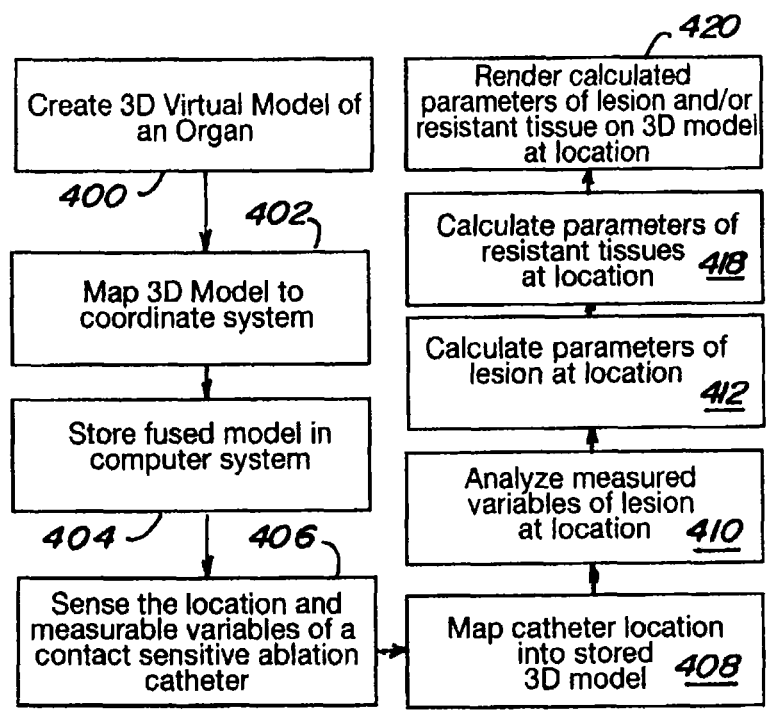
FIG. 26 depicts a flow chart of the steps for generating and displaying edema or resistive tissue on a 3D model of an organ according to one embodiment of the invention.

Referring to FIGS. 25 and 26, methods of characterizing and visualizing lesions according to embodiments of the invention are presented. First, a 3D model of the physical organ such as a heart is created utilizing MRI, CT scan, sonogram, electrical or magnetic impulse is generated 400.

The 3D virtual model of an organ is then mapped to a coordinate system thus fusing directional coordinates with the 3D virtual model 402. The fused 3D model is then stored in memory 404. In certain embodiments the fused 3D model is stored in an HIS 200 and linked with the patient's medical history. In other embodiments, the fused model is utilized only in a data acquisition and processing unit 124 for use during the ablation procedure. During the ablation procedure, the location and measurable variables of a contact sensitive ablation catheter are recorded 406.

In certain embodiments, measurable variables include time, temperature, force, power, contact, electrical impedance and location. The measured location of the catheter is then mapped onto the stored 3D model 408. The fused 3D model may be transferred from the HIS 200 to a data acquisition and processing unit 124 before the procedure begins. In other embodiments, the fused 3D model is resident in the data acquisition and processing unit 124. Next a data acquisition and processing unit 124 will analyze the measured variables of the lesion at the current catheter location 410. In certain embodiments, the data acquisition and processing unit 124 will estimate the time-force integral based on the measured variables. The data acquisition and processing unit 124 will then calculate the parameters of the lesion at the location. In various embodiments parameters may include area, depth or volume or any combination of the forgoing of the lesion at the location 412. In other embodiments, the data acquisition and processing unit 124 will also calculate visual effects to be used in the visualization of the calculated parameters of the lesion at the location. The visual effects may include varying color, stroke or gradient fill effects. The data acquisition and processing unit 124 will then render the calculated parameters of the lesion at the location on the 3D model 414. In certain embodiments, an additional step of calculating the parameters of resistant tissues is performed 416. The data acquisition and processing unit 124 will then render the calculated parameters of the lesion, the resistant tissue or a combination on the 3D model 418. In this embodiment, the visualization of the resistive tissue will utilize a significantly different visual effect than the effects used to visualize lesion information.

Each of the features and methods disclosed herein may be used separately, or in conjunction with other features and methods, to provide improved devices, systems and methods for making and using the same. Therefore, combinations of features and methods disclosed herein may not be necessary to practice the invention in its broadest sense and are instead disclosed merely to particularly describe representative embodiments of the invention.

For purposes of interpreting the claims for the present invention, it is expressly intended that the provisions of Section 112, sixth paragraph of 35 U.S.C. are not to be invoked unless the specific terms "means for" or "steps for" are recited in the subject claim.

What is claimed is:

1. A system for ablating a target tissue during a medical procedure, the system comprising:
   an elongate flexible catheter adapted to be introduced into a patient during said medical procedure, said catheter including a distal portion;
   an ablation head disposed at said distal portion of said catheter, said ablation head adapted to contact with said target tissue during said medical procedure;
   a force sensor operatively coupled with said ablation head for measurement of a contact force exerted on said ablation head, said force sensor configured to output a signal in response to said contact force;
   a power source operatively coupled with said ablation head for energization of said ablation head; and
   a control system configured to receive said signal from said force sensor and to produce a sequence of contact force values acquired over a time period of energization based on said signal output by said force sensor for calculation of a force-time integral that is utilized by said control system to control ablation of said target tissue.

2. The system of claim 1 wherein said force-time integral is one of a force over time integral, a force-energization over time integral and a force time product.

3. The system of claim 1 wherein said control system is adapted to determine a magnitude of an energization parameter delivered to said ablation head and to predict a size parameter of a lesion on said target tissue created by said energization parameter, said prediction being based on said force-time integral and said magnitude of said energization parameter, said energization parameter being one of power and electrical current.

4. The system of claim 3, wherein said size parameter is one of lesion volume and lesion depth.

5. The system of claim 3 wherein said energization parameter is said electrical current and said control system further comprises a current sensor adapted to detect said electrical current to said ablation head.

6. The system of claim 1 wherein said control system is adapted to control said time period of energization of said ablation head.

7. The system of claim 1 wherein said control system is adapted to control a magnitude of an energization parameter delivered to said ablation head with said power source.

8. The system of claim 1 wherein said control system is adapted to control a magnitude of an energization parameter delivered to said ablation head with said power source, said magnitude of said energization parameter being based on the magnitude of said contact force.

9. The system of claim 1 further comprising a robotic manipulator for movement of said distal portion of said catheter.

10. The system of claim 9 wherein said robotic manipulator is controlled by said control system.

11. The system of claim 1 wherein said force-time integral is calculated in real time.

12. The system of claim 11 wherein said control system is adapted to substantially disable energization of said ablation head with said power source when said force-time integral reaches a predetermined value.

13. The system of claim 1 wherein said control system includes a central processor that computes said force-time integral.

14. The system of claim 13 wherein said central processor is adapted for said production of said sequence of contact force values.

15. The system of claim 13 wherein said control system includes a force signal conditioning system adapted to digitize said signal received from said force sensor and to provide the digitized signal to said central processor.

16. The system of claim 15 wherein said force sensor includes a fiber optic strain gauge and said force signal conditioning system includes a fiber optic interrogator operatively coupled with said fiber optic strain gauge and said central processor.

17. The system of claim 15 wherein said force signal conditioning system is adapted for said production of said sequence of contact force values.

18. The system of claim 15 wherein said force-time integral is based on one of a pressure and a strain measurement.

19. A system for delivering energy to a target tissue during a medical procedure, the system comprising:
- an elongate flexible catheter adapted to be introduced into a patient during said medical procedure, said catheter including a distal portion;
- an ablation head disposed at said distal portion of said catheter and arranged to contact said target tissue during said medical procedure;
- a force sensor operatively coupled with said ablation head for detection of a contact force exerted on said ablation head, said force sensor adapted produce an output that correlates with said contact force;
- a power source operatively coupled with said ablation head for energization of said ablation head; and
- a control system including a central processor and being operatively coupled to said force sensor and said power source, said central processor having access to a storage medium that contains programming instructions to be carried out by the central processor, said programming instructions comprising:
  - measuring a sequence of contact forces with said force sensor while said ablation head is in contact with said target tissue, said sequence of contact forces being in reaction to said contact;
  - energizing said ablation head for a period of time while said sequence of contact forces is being measured; and
  - determining a force-time integral based on said sequence of contact forces that were measured with said force sensor over said period of time of energizing said ablation head.

20. The system of claim 19 wherein said programming instructions further comprise estimating a size parameter of a lesion based on said force-time integral.

21. The system of claim 19 wherein said programming instructions include:
- determining a magnitude of an energization parameter delivered to said ablation head during said energizing of said ablation head; and
- determining a size parameter of a lesion based on said force-time integral and said magnitude of said energization parameter.

22. The system of claim 21 wherein:
- said energization parameter is electrical current;
- said control system includes a current sensor adapted to determine said magnitude of said energization parameter; and
- said programming instructions further comprise measuring said electrical current delivered to said ablation head during said energizing of said ablation head.

23. The system of claim 21 wherein said programming instructions include controlling said magnitude of said energization parameter during said energizing of said ablation head.

24. The system of claim 23 wherein the magnitude of said energization parameter is selected based on the contact forces of said sequence of contact forces to prevent or reduce the incidence of steam pop.

25. The system of claim 19 wherein said control system further comprises a current sensor adapted to detect energization of said ablation head.

26. The system of claim 19 wherein said force-time integral is determined in real time.

27. The system of claim 26 wherein said programming instructions further comprise terminating energization of said ablation head when said force-time integral reaches a predetermined value.

28. The system of claim 19 wherein said control system includes a force signal conditioning system adapted to digitize said output received from said force sensor and to provide the digitized signal to said central processor.

29. The system of claim 28 wherein said force sensor includes a fiber optic strain gauge and said force signal conditioning system includes a fiber optic interrogator operatively coupled with said fiber optic strain gauge and said central processor.

30. The system of claim 29 wherein said force signal conditioning system is configured for said measuring of said sequence of contact forces and providing said sequence of forces to said central processor.

* * * * *